(12) United States Patent
Gorman et al.

(10) Patent No.: US 6,767,996 B1
(45) Date of Patent: Jul. 27, 2004

(54) ALTERED ANTIBODIES AND THEIR PREPARATION

(75) Inventors: Scott David Gorman, Cambridge (GB); Michael Ronald Clark, Cambridge (GB); Stephen Paul Cobbold, Cambridge (GB); Herman Waldmann, Cambridge (GB)

(73) Assignee: Glaxo Wellcome Inc., Research Triangle Park, NC (US)

( * ) Notice: Subject to any disclaimer, the term of this patent is extended or adjusted under 35 U.S.C. 154(b) by 0 days.

(21) Appl. No.: 08/030,175

(22) PCT Filed: Sep. 16, 1991

(86) PCT No.: PCT/GB91/01578

§ 371 (c)(1),
(2), (4) Date: May 17, 1993

(87) PCT Pub. No.: WO92/05274

PCT Pub. Date: Apr. 2, 1992

(30) Foreign Application Priority Data

Sep. 17, 1990 (GB) .............................. 9020282

(51) Int. Cl.[7] .......................... C07K 16/00; C12P 21/04; C12P 21/08; C07H 21/04
(52) U.S. Cl. ............................... 530/387.3; 530/387.1; 530/387.7; 530/388.22; 530/388.75; 530/388.7; 530/389.6; 435/69.7; 536/23.4; 536/23.53
(58) Field of Search ...................... 424/85.8; 435/70.21, 435/172.2, 69.7, 240.27, 252.3, 320.1, 240.1; 530/300, 328, 329, 330, 326, 327, 867, 387.3, 387.1, 387.7, 388.75, 389.7, 389.6, 388.22; 536/23.4, 23.53

(56) References Cited

U.S. PATENT DOCUMENTS

| 4,652,447 A | 3/1987 | Kung et al. ................. 424/85 |
| 4,695,459 A | 9/1987 | Steinman .................... 424/95 |

FOREIGN PATENT DOCUMENTS

| EP | 200412 | 10/1986 |
| EP | 239400 | 9/1987 |
| EP | 328404 | 2/1989 |
| EP | 365209 | 10/1989 |
| EP | 380018 | 1/1990 |
| EP | 409242 | 7/1990 |
| EP | 403156 | 12/1990 |
| WO | 8601533 | 3/1986 |
| WO | 9007861 | 7/1990 |
| WO | 9107492 | 5/1991 |
| WO | 9109966 | 7/1991 |
| WO | 9109967 | 7/1991 |

OTHER PUBLICATIONS

Mathieson et al N. Eng. J. Mel 323:250–254 1990.*
Harris et al TibTech 11:42–46 1993.*
Osband et al Imm. Today 11:193–195 1990.*
Dillman et al Ann. Int. Med. 111:592–603 1989.*
Hird et al Genes & Cancer 1990 Wiley & Sons Pub Ch 17.*
Waldmann 252: 1657–1661 1991.*
Roberts et al., *Nature, 328*, 1987, pp.731–734.
Sharon, *Proc. Natl. Acad. Sci. USA, 87*, 1990, pp. 4814–4817.
Tao, et al., *Journal of Immunology, 143*(8), 1989, pp. 2595–2601.
Verhoeyen et al., *Science, 239*, 1988, pp. 1534–1536.
Waldmann, *Science, 252*, 1991, pp. 1657–1662.
Ward et al., *Nature, 341*, 1989, pp. 544–546.
Jones et al., *Nature, 321* (1986), pp. 522–525.
Lazar et al., *Molecular and Cellular Biology, 8*(3), 1247–1252, 1988.
Bruggemann, et al., *J. Exp. Med.*, 1987, pp. 1351–1361.
Burgess, et al., *The Journal of Cell Biology, 111* (1990), pp. 2129–2138.
Byrn et al., *Nature, 344*, 1990, pp. 667–670.
Crowe et al., *Nucleic Acid Research, 17*, 1989, p. 7992.
Daugherty et al., *Nucleic Acids Research, 19*, 1991, pp. 2471–2476.
Gorman et al., *Proc. Natl. Acad. Sci. USA, 88*, 1991, pp. 4181–4185.
Kettleborough, et al., *Protein Engineering, 4:7*, 1991, pp. 773–784 (ABST.).
Lewis, et al., *Gene, 101*, 1991, pp. 297–302.
Orlandi et al., *Proc. Natl. Acad. Sci. USA, 86*, 1989, pp. 3833–3847.
Queen et al., *Proc. Natl. Acad. Sci. USA, 86*, 1989, pp. 10029–10033.
Reichmann, L., et al., *Nature, 332*, 1988, 323–327.

* cited by examiner

Primary Examiner—Donald E. Adams
(74) Attorney, Agent, or Firm—Nixon & Vanderhye P.C.

(57) ABSTRACT

An altered antibody chain is produced in which the CDR's of the variable domain of the chain are derived from a first mammalian species. The framework-encoding regions of DNA encoding the variable domain of the first species are mutated so that the mutated framework-encoding regions encode a framework derived from a second different mammalian species. The or each constant domain of the antibody chain, if present, are also derived from the second mammalian species.

11 Claims, 33 Drawing Sheets

Fig. 1

Figure 13:
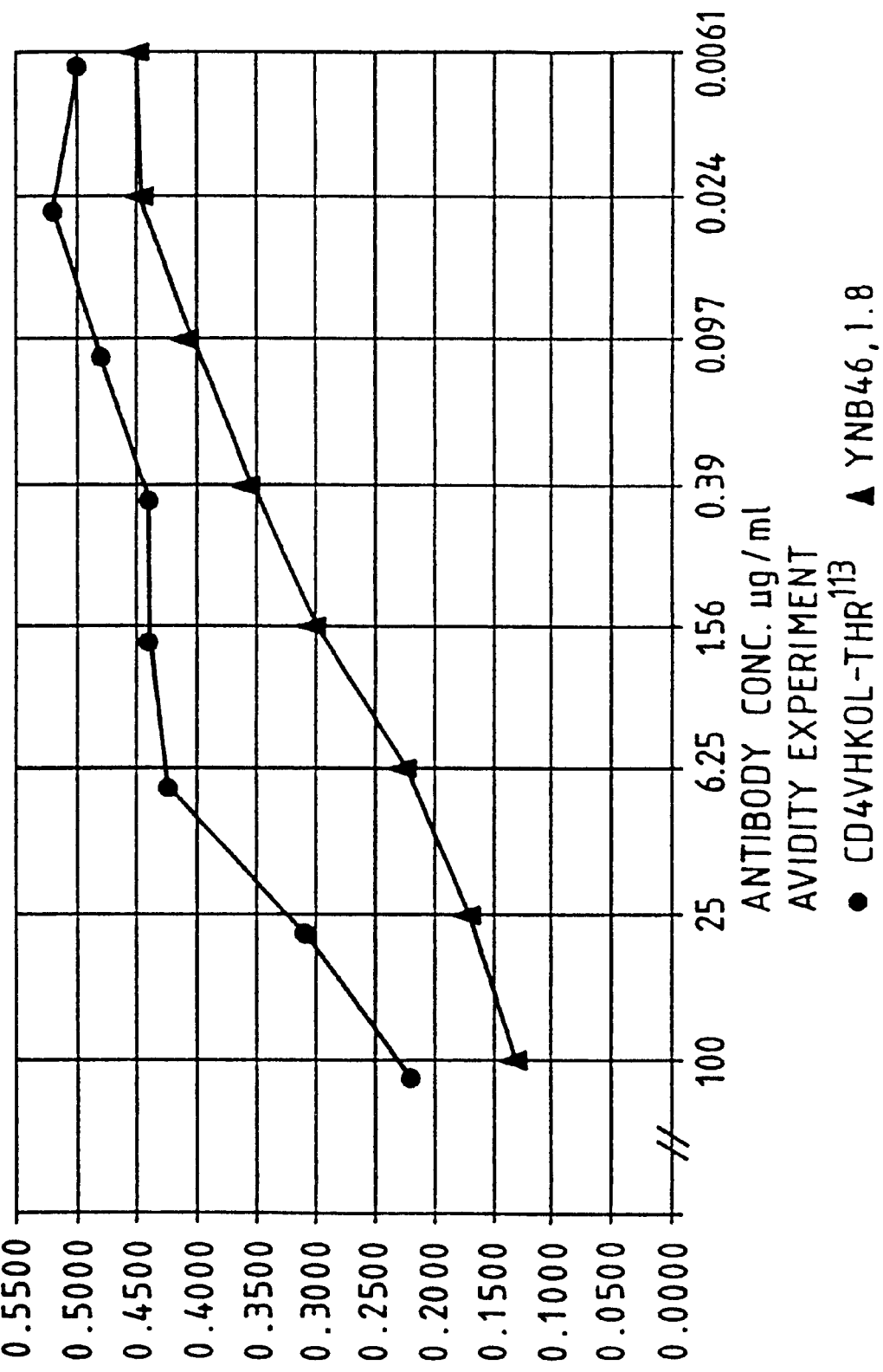

```
        HindIII
1       AAGCTTATGAATATGCAAATCCTCTGAATCTACAGTGTAAATATAGGTTTGTCTATACC     59

60      ACAAACAGAAAAACATGAGATCACAGTTCTCTCTACAGTTACTGAGCACACAGGACCTCA    119

-19               M  G  W  S  C  I  I  L  F  L  V  A  T  A  T           -5
120     CCATGGGATGGAGCTGTATCATCCTCTTCTTGGTAGCAACAGCTACAGGTAAGGGGTGCA    179

180     CAGTAGCCAGGCTTGAGGTCTCGGACATATATATGGGTGACAATGACATCCACTTTGCCTTT  239

-4                G  V  H  S  D  I  Q  L  T  Q  S  P  V  S  L  S  A      13
240     CTCTCCACAGGTCTCCACTCCGACATCCAGCTGACCCAGTCTCCAGTTTCCCTGTCTGCA    299

14          S  L  G  E  T  V  N  I  E  C  L  A  S  E  D  I  Y  S  D  L    33
                                          CDR1
300     TCTCTGGGAGAAACTGTCAACATCGAATGTCTAGCAAGTGAGGACATTTACAGTGATTTA    359
```

Fig. 1A

```
34         A   W   Y   Q   Q   K   P   G   K   S   P   Q   L   L   I   Y   N   T   D   T    53
                                                                           ┌─────────────┐
                                                                           │   CDR 2     │
                                                                           └─────────────┘
360  GCATGGTATCAGCAGAAGCCAGGGAAATCTCCTCAACTCCTGATCTATAATACAGATACC          419

54     L   Q   N   G   V   P   S   R   F   S   G   S   G   S   G   T   Q   Y   S   L     73
     ┌───────────┐
     │           │
     └───────────┘
420  TTGCAAAATGGGGTCCCCTTCACGGTTAGTGGCAGTGGATCTGGCACACAGTATTCTCTA          479

74     K   I   N   S   L   Q   S   E   D   V   A   T   Y   F   C   Q   Q   Y   N   N     93
                                                                       ┌─────────────────
                                                                       │    CDR 3
                                                                       └─────────────────
480  AAAATAAACAGCCTGCAATCTGAAGATGTCGCCACTTATTTCTGTCAACAATATAACAAT          539

94     Y   P   W   T   F   G   G   G   T   K   L   E   I   K   R                         108
     ──────────────┐
                   │
     ──────────────┘
540  TATCCGTGGACGTTCGGTGGAGGGACCAAGCTGGAGATCAAACGTGAGTAGAATTTAAAC          599

BamHI
600  TTTGCTTCCTCAGTTGGATCC                                                620
```

Fig. 2

```
                                                            M  G  W  S  C  I   -14
 -19  HindIII
   1  AAGCTTGGCTCTACAGTTACTGAGCACACAGGACCTCACCATGGGATGGAGCTGTATC    58

I  L  F  L  V  A  T  A  T  G  V  H  S  D  I  Q  M  T  Q  S    7
 -13
  59  ATCCTCTTCTTGGTAGCAACAGCTACAGGTGTCCACTCCGACATCCAGATGACCCAGAGC  118

P  S  S  L  S  A  S  V  G  D  R  V  T  I  T  C │K  A  S  Q│  27
                                                    │  CDR 1   │
   8
 119  CCAAGCAGCCTGAGCGCCAGCGTGGGTGACAGAGTCACCATCACCTGT│AAGGCAAGTCAG│ 178

│N  I  D  K  Y  L  N│ W  Y  Q  Q  K  P  G  K  A  P  K  L  L   47
     │      CDR 2        │
  28
 179 │AATATTGACAAATACTTAAAC│TGGTACCAGCAGAAGCCAGGTAAAGCTCCAAAGCTGCTG  238

I  Y │N  T  N  N  L  Q  T│ G  V  P  S  R  F  S  G  S  G  S   67
           │     CDR           │
  48
 239  ATCTAC│AATACAAATAACTTGCAAACA│GGGGTGCCAAGCAGATTCAGCGGTAGCGGTAGC 298

G  T  D  F  F  F  T  I  S  S  L  Q  P  E  D  I  A  T  Y  Y   87
  68
 299  GGTACCGACTTCACCTTCACCATCAGCCTTCAGCCCAGAGGACATCGCCACCTACTAC    358
```

Fig. 2A

```
            CDR 3
      ┌─────────────────────┐
 88   C  L  Q  H  I  S  R  P  R  T   F  G  Q  G  T  K  V  E  I  K    107
359   TGCTTGCAGCATATAAGTAGCCCGCGCACGTTCGGCCAAGGGACCAAGGTGGAAATCAAA    418

108   R  T  V  A  A  P  S  V  F  I  F  P  P  S  D  E  Q  L  K  S     127
419   CGAACTGTGGCTGCACCAGCCATCTGTCTTCATCTTCCCGCCATCTGATGAGCAGTTGAAATCT    478

128   G  T  A  S  V  V  C  L  L  N  N  F  Y  P  R  E  A  K  V  Q     147
479   GGAACTGCCTCTGTTGTGTGCCTGCTGAATAACTTCTATCCCAGAGAGGCCAAAGTACAG    538

148   W  K  V  D  N  A  L  Q  S  G  N  S  Q  E  S  V  T  E  Q  D     167
539   TGGAAGGTGGATAACGCCCTCCAATCGGGTAACTCCCAGGAGAGTGTCACAGAGCAGGAC    598

168   S  K  D  S  T  Y  S  L  S  S  T  L  T  L  S  K  A  D  Y  E     187
599   AGCAAGGACAGCACCTACAGCCTCAGCAGCACCCTGACGCTGAGCAAAGCAGACTACGAG    658

188   K  H  K  V  Y  A  C  E  V  T  H  Q  G  L  S  S  P  V  T  K     207
659   AAACACAAAGTCTACGCCTGCGAAGTCACCCATCAGGGCCTGAGCTCGCCCGTCACAAAG    718

208   S  F  N  R  G  E  C Trm HindIII                                 214
719   AGCTTCAACAGGGGAGAGTGTTAGAAGCTT                                   748
```

Fig. 3

```
                                                     M  G  W  S  C  I          -14
      HindIII
  1   AAGCTTGGCCTCTACAGTTACTGAGCACACAGGACCTTCACCATGGGATGGAGCTGTATC              58

-13  I  L  F  L  V  A  T  A  T  G  V  H  S  D  I  Q  M  T  Q  S             7
  59      ATCCTCTTCTTGGTAGCAACAGCTACAGGTGTCCACTCCGACATCCAGATGACCCAGAGC          118

8  P  S  S  L  S  A  S  V  G  D  R  V  T  I  T  C │ L  A  S  E           27
 119      CCAAGCAGCCTGAGCGCCAGCGTGGGTGACAGAGTGACCATCACCTGT  CTAGCAAGTGAG        178
                                                          CDR 1

28  D  I  Y  S  D  L  A │W  Y  Q  Q  K  P  G  K  A  P  K  L  L           47
 179   │  GACATTTACAGTGATTTAGCA│TGGTACCAGCAGAAGCCAGGTAAAGGCTCCAAAGCTCTG        238
        CDR 2

48  I  Y │ N  T  D  T  L  Q │ N  G  V  P  S  R  F  S  G  S  G  S           67
 239     ATCTAC│ AATACAGATACCTTGCAA│AATGGTGTGCCAAGCAGATTCAGCGGTAGCGGTAGC       298

68  G  T  D  F  F  F  T  I  S  S  L  Q  P  E  D  I  A  T  Y  Y           87
 299      GGTACCGACTTCTTCACCATCAGCAGCCTCCAGCCAGAGGACATCGCCACCTACTAC            358

88  C │ Q  Q  Y  N  N  Y  P  W  T │ F  G  Q  G  T  K  V  E  I  K         107
 359      TGC│CAACAGTATAACAATTATCCGTGGACG│TTCGGCCAAGGGACCAAGGTGGAAATCAAA      418
                        CDR 3
```

Fig. 3A

```
108  R  T  V  A  A  P  S  V  F  I  F  P  P  S  D  E  Q  L  K  S   127
419  CGAACTGTGGCTGCCACCATCTGTCTTCCCGCCATCTGATGAGCAGTTGAAATCT        478

128  G  T  A  S  V  V  C  L  L  N  N  F  Y  P  R  E  A  K  V  Q   147
479  GGAACTGCCTCTGTGTGTGCCTGCTGAATAACTTCTATCCCAGAGAGGCCAAAGTACAG    538

148  W  K  V  D  N  A  L  Q  S  G  N  S  Q  E  S  V  T  E  Q  D   167
539  TGGAAGGTGGATAACGCCCTCCAATCGGGTAACTCCCAGGAGAGTGTCACAGAGCAGGAC   598

168  S  K  D  S  T  Y  S  L  S  S  T  L  T  L  S  K  A  D  Y  E   187
599  AGCAAGGACAGCACCTACAGCCTCAGCAGCACCCTGACGCTGAGCAAAGCAGACTACGAG   658

188  K  H  K  V  Y  A  C  E  V  T  H  Q  G  L  S  S  P  V  T  K   207
659  AAACACAAAGTCTACGCCTGCGAAGTCACCCATCAGGGCCTGAGCTCGCCCGTCACAAAG   718

208  S  F  N  R  G  E  C  Trm  HindIII                             214
719  AGCTTCAACAGGGGAGAGTGTTAGAAGCTT                                 748
```

Fig. 4

```
        HindIII
1       AAGCTTATGAATATGCAAATCCCTGAATCTACACATGTAAATATAGGTTTGTCTATACC              59

60      ACAAACAGAAAAACATGAGATCACAGTTCTCTCTACAGTTACTCAGCACACAGGACCTCA             119

M  G  W  S  C  I  I  L  F  L  V  A  T  A  T                    -5
120     CCATGGGATGGAGCTGTATCATCCTCTTCTTGGTAGCAACAGCTACAGGTAAGGGGCTCA            179

239
180     CAGTAGCAGGCTTGAGGTCTGGACATATATGGGTGACAATGACATCCACTTTGCCCTTT             239

G  V  H  S  Q  V  Q  L  Q  E  S  G  G  G  L  V  Q              13
240     CTCTCCACAGGTGTCCACTCCCAGGTCCAGCTGCAGGAGTCTGGTGGAGGCTTAGTGCAG            299

┌─CDR 1──┐
         P  G  R  S  L  K  L  S  C  A  A  S  G  L  T  F  S  │ N  Y  │ G         33
300     CCTGGAAGGTCCCTGAAACTCTCCTGTGCAGCCTCTGGACTCACTTTCAGTAACTATGGC            359

┌──CDR 2──┐
                M │ A │ W  V  R  Q  A  P  T  K  G  L  E  W  V  A │ T  I  S  H  │   53
360     ATGGCCTGGGTCCGCCAGGCTCCAGGGAAGGGGCTGGAGTGGGTCGCAACCATTAGTCAT            419
```

Fig. 4A

```
 54      D  G  S  D  T  Y  F  R  D  S  V  K  G  R  F  T  I  S  R  D      73
420   GATGGTAGTGACACTTACTTTCGAGACTCCGTGAAGGGCCGATTCACTATCTCCAGAGAT       479

74      N  G  K  S  T  L  Y  L  Q  M  D  S  L  R  S  E  D  T  A  T      93
480   AATGGAAAAGCACCCTATACCTGCAAATGGACAGTCTGAGGTCTGAGGACACGGCCACT        539

94      Y  Y  C  A  R  Q  G  T  I  A  G  I  R  H  W  G  Q  G  T  T     113
540   TATTACTGTGCAAGACAAGGACTATAGCAGGTATACGTCACTGGGCCAAGGGACCACG         599

114      V  T  V  S  S                                                  118
600   GTCACCGTCTCCTCAGGTGAGTCCTTACAACCTCTCTCTTCTATTCAGCTTAAATAGATT       659

660   TTACTGCATTTGTTGGGGGGAAATGTGTATCTGAATTTCAGGTCATGAAGGACTAGG          719

720   GACACCTTGGGAGTCAGAAAGGGTCATTGGGAGCCCCGGGCTGATGCCAGACAGACATCCTC    779

BamHI
780   AGCTCCCAGACTTCATGGCCAGAGATTTATAGGATCC                              817
```

Fig. 5

```
                                      M  G  W  S  C  I  I  L           -12
        HindIII
  -19   AAGCTTTACAGTTACTGAGCACACAGGACCTCACCATGGAGCTGTATCATCCTC            59
    1

F  L  V  A  T  A  T  G  V  H  S  Q  V  Q  L  Q  E  S  G  P        9
  -11   TTCTTGGTAGCAACAGCTACAGTGTCCACTCCCAGGTCCAACTGCAGGAGAGCGGTCCA       119
   60

G  L  V  R  P  S  Q  T  L  S  L  T  C  T  V  S  G  F  T  F       29
   10   GGTCTTGTGAGACCTAGCCAGACCCTGAGCCTGACCTGCACCGTGTCTGGCTTCACCTTC      179
  120
                                       ┌──────────────┐
        T  D  F  Y  M  N │ W  V  R  Q  P  P  G  R  G  L  E  W  I  G       49
                        │                                    
   30   ACCGATTTCTACATGAAC TGGGTGAGACAGCCACCTGGACGAGGTCTTGAGTGGATTGGA     239
  180                  CDR 1

┌──────────────────────────────────────────┐
        F  I  R  D  K  A  K  G  Y  T  T  E  Y  N  P  S  V  K  G │ R       69

50   TTTATTAGAGACAAAGCTAAAGGTTACACAACAGAGTACAATCCATCTGTGAAGGGGAGA      299
  240                              CDR 2
```

Fig. 5A

```
           V  T  M  L  V  D  T  S  K  N  Q  F  S  L  R  L  S  S  V  T        89
 70
300  GTGACAATGCTGGTAGACACCAGCAAGAACCAGTTCAGCCTGAGACTCAGCAGCGTGACA            359

A  A  D  T  A  V  Y  Y  C  A  R  E  G  H  T  A  A  P  F  D       109
 90                                            |_____
360  GCCGCCGACACCGCGGTCTATTATTGTGCAAGAGAGGGCCACACTGCTGCCTTTTGAT              419
                                               CDR 3

Y  W  G  Q  G  S  L  V  T  V  S  S  A  S  T  K  G  P  S  V       129
110  __|
420  TACTGGGGTCAAGGCAGTCTCGTCACAGTCTCCTCAGCCTCCACCAAGGGCCCATCGGTC            479

F  P  L  A  P  S  S  K  S  T  S  G  G  T  A  A  L  G  C  L       149
130
480  TTCCCCCTGGCACCCTCCTCCAAGAGCACCTCTGGGGGCACAGCGGCCCTGGGCTGCCTG            539

V  K  D  Y  F  P  E  P  V  T  V  S  W  N  S  G  A  L  T  S       169
150
540  GTCAAGGACTACTTCCCCGAACCGGTGACGGTGTCGTGGAACTCAGGCGCCCTGACCAGC            599
```

Fig. 5B

```
170  G   V   H   T   F   P   A   V   L   Q   S   S   G   L   Y   S   L   S   S   V    189
600  GGCGTGCACACCTTCCCGGCTGTCCTACAGTCCTCAGGACTCTACTCCCTCAGCAGCGTG          659

190  V   T   V   P   S   S   S   L   G   T   Q   T   Y   I   C   N   V   N   H   K    209
660  GTGACCGTGCCCTCCAGCAGCTTGGGCACCCAGACCTACATCTGCAACGTGAATCACAAG          719

210  P   S   N   T   K   V   D   K   K   V   E   P   K   S   C   D   K   T   H   T    229
720  CCCAGCAACACCAAGGTGGACAAGAAAGTTGAGCCCAAATCTTGTGACAAAACTCACACA          779

230  C   P   P   C   P   A   P   E   L   L   G   G   P   S   V   F   L   F   P   P    249
780  TGCCCACCGTGCCCAGCACCTGAACTCCTGGGGGGACCGTCAGTCTTCCTCTTCCCCCCA          839

250  K   P   K   D   T   L   M   I   S   R   T   P   E   V   T   C   V   V   V   D    269
840  AAACCCAAGGACACCCTCATGATCTCCCGGACCCCTGAGGTCACATGCGTGGTGGTGGAC          899
```

Fig. 5C

```
270  V   S   H   E   D   P   E   V   K   F   N   W   Y   V   D   G   V   E   V   H        289
900  GTGAGCCACGAAGACCCTGAGGTCAAGTTCAACTGGTACGTGGACGGCGTGGAGGTGCAT              959

290  N   A   K   T   K   P   R   E   E   Q   Y   N   S   T   Y   R   V   V   S   V        309
960  AATGCCAAGACAAAGCCGCGGGAGGAGCAGTACAACAGCACGTACCGTGTGGTCAGCGTC             1019

310  L   T   V   L   H   Q   D   W   L   N   G   K   E   Y   K   C   K   V   S   N        329
1020 CTCACCGTCCTGCACCAGGACTGGCTGAATGGCAAGGAGTACAAGTGCAAGGTCTCCAAC             1079

330  K   A   L   P   A   P   I   E   K   T   I   S   K   A   K   G   Q   P   R   E        349
1080 AAAGCCCTCCCAGCCCCCATCGAGAAAACCATCTCCAAAGCCAAAGGGCAGCCCCGAGAA             1139

350  P   Q   V   Y   T   L   P   P   S   R   D   E   L   T   K   N   Q   V   S   L        369
1140 CCACAGGTGTACACCCTGCCCCCATCCCGGGATGAGCTGACCAAGAACCAGGTCAGCCTG             1199
```

Fig. 5D

```
370  T   C   L   V   K   G   F   Y   P   S   D   I   A   V   E   W   E   S   N   G    389
1200 ACCTGCCTGGTCAAAGGCTTCTATCCCAGCGACATCGCCGTGGAGTGGGAGAGCAATGGG          1259

390  Q   P   E   N   N   Y   K   T   T   P   P   V   L   D   S   D   G   S   F   F    409
1260 CAGCCCGAGAACAACTACAAGACCACCCCGCCTCCCGTGCTGGACTCCGACGGCTCCTTCTTC      1319

410  L   Y   S   K   L   T   V   D   K   S   R   W   Q   Q   G   N   V   F   S   C    429
1320 CTCTACAGCAAGCTCACCGTGGACAAGAGCAGGTGGCAGCAGGGGAACGTCTTCTCATGC         1379

430  S   V   M   H   E   A   L   H   N   H   Y   T   Q   K   S   L   S   L   S   P    448
1380 TCCGTGATGCATGAGGCTCTGCACAACCACTACACGCAGAAGAGCCTCTCCCTGTCTCCG         1439

449  G   K   Trm                                HindIII                                 450
1440 GGTAAATGAGTGCCGACGGCCCCAAGCTT                                                     1467
```

Fig. 6

```
                                                    M  G  W  S  C  I  I  L      -12
     HindIII
-19  AAGCTTACAGTTACTGAGCACACAGGACCTCACCATGGGATGGAGCTGTATCATCCTC                   59
1

F  L  V  A  T  A  T  G  V  H  S  Q  V  Q  L  Q  E  S  G  P                 9
-11  TTCTTGGTAGCAACAGCTACAGGTGTCCACTCCCAGGTCCAACTGCAGGAGAGCGGGTCCA               119
60

G  L  V  R  P  S  Q  T  L  S  L  T  C  T  V  S  G  F  T  F                 29
10   GGTCTTGTGAGACCCTAGCCAGACCCTGAGCCTGACCTGCACCGTGTCTGGCTTCACCTTC              179
120                                                       ┌──
                                                          │ T
                                                          CDR 1

T  N  Y  G  M  A   W  V  R  Q  P  P  G  R  G  L  E  W  I  G              49
30    ACCAACTATGGCATGGCC TGGGTGAGACAGCCACCTGGACGAGGTCTTGAGTGGATTGGA             239
180   N  Y  G  M  A │
      ──────────────┘
      CDR 1
                                    ┌── T  I  S  H  D  G  S  D  T  Y  F  R  D  S  V  K  G  R  V  T    69
50                                  │   ACCATTAGTCATGATGGTAGTGACACTTACTTTCGAGACTCTGTGAAGGGGAGAGTGACA  299
240                                 CDR 2
```

Fig. 6A

```
 70   M  L  V  D  T  S  K  N  Q  F  S  L  R  L  S  S  V  T  A  A                        89
300  ATGCTGGTAGACACCAGCAAGAACCAGTTCAGCCTGAGACTCAGCAGCGTGACAGCCGCC                       359

90   D  T  A  V  Y  Y  C  A  R  |Q  G  T  I  A  G  I  R  H| W  G                      109
360  GACACCGCGGTCTATTATTGTGCAAGACAAGGCACTATAGCTGGTATACGTCACTGGGGT                       419
                                 ─────────────CDR 3─────────

110   Q  G  S  L  V  T  V  S  S  A  S  T  K  G  P  S  V  F  P  L                      129
420  CAAGGCCAGCCTCGTCACAGTCTCCTCAGCCTCCACCAAGGGCCCATCGGTCTTCCCCCTG                      479

130   A  P  S  S  K  S  T  S  G  G  T  A  A  L  G  C  L  V  K  D                      149
480  GCACCCTCCTCCAAGAGCACCTCTGGGGGCACAGCGGCCCTGGGCTGCCTGGTCAAGGAC                       539

150   Y  F  P  E  P  V  T  V  S  W  N  S  G  A  L  T  S  G  V  H                      169
540  TACTTCCCCGAACCGGTGACGGTGTCGTGGAACTCAGGCGCCCTGACCAGCGGCGTGCAC                       599
```

Fig. 6B

```
170  T  F  P  A  V  L  Q  S  S  G  L  Y  S  L  S  S  V  V  T  V   189
600  ACCTTCCCGGCTGTCCTACAGTCCTCAGGACTCTACTCCCTCAGCAGGTGTGACCGTG    659

190  P  S  S  S  L  G  T  Q  T  Y  I  C  N  V  N  H  K  P  S  N   209
660  CCCTCCAGCAGCTTGGGCACCCAGACCTACATCTGCAACGTGAATCACAAGCCCAGCAAC  719

210  T  K  V  D  K  K  V  E  P  K  S  C  D  K  T  H  T  C  P  P   229
720  ACCAAGGTGGACAAGAAAGTTGAGCCCAAATCTTGTGACAAACTCACACATGCCCACCG   779

230  C  P  A  P  E  L  L  G  G  P  S  V  F  L  F  P  P  K  P  K   249
780  TGCCCCAGCACCTGAACTCCTGGGGGACCGTCAGTCTTCCTCTTCCCCCAAAACCCAAG   839

250  D  T  L  M  I  S  R  T  P  E  V  T  C  V  V  V  D  V  S  H   269
840  GACACCCTCATGATCTCCCGGACCCCTGAGGTCACATGCGTGGTGGTGGACGTGAGCCAC  899
```

Fig. 6C

```
270  E   D   P   E   V   K   F   N   W   Y   V   D   G   V   E   V   H   N   A   K    289
900  GAAGACCCTGAGGTCAAGTTCAACTGGTACGTGGACGGCGTGGAGGTGCATAATGCCAAG      959

290  T   K   P   R   E   E   Q   Y   N   S   T   Y   R   V   V   S   V   L   T   V    309
960  ACAAAGCCGCGGGAGGAGCAGTACAACAGCACGTACCGTGTGGTCAGCGTCCTCACCGTC     1019

310  L   H   Q   D   W   L   N   G   K   E   Y   K   C   K   V   S   N   K   A   L    329
1020 CTGCACCAGGACTGGCTGAATGGCAAGGAGTACAAGTGCAAGGTCTCCAACAAGCCCTC      1079

330  P   A   P   I   E   K   T   I   S   K   A   K   G   Q   P   R   E   P   Q   V    349
1080 CCAGCCCCCATCGAGAAAACCATCTCCAAAGCCAAAGGGCAGCCCCGAGAACCACAGGTG     1139

350  Y   T   L   P   P   S   R   D   E   L   T   K   N   Q   V   S   L   T   C   L    369
1140 TACACCCTGCCCCCATCCCGGGATGAGCTGACCAAGAACCAGGTCAGCCTGACCTGCCTG     1199
```

Fig. 6D

```
370   V   K   G   F   Y   P   S   D   I   A   V   E   W   E   S   N   G   Q   P   E          389
1200  GTCAAAGGCTTCTATCCCAGCGACATCGCCGTGGAGTGGGAGAGCAATGGGCAGCCGGAG          1259

390   N   N   Y   K   T   T   P   P   V   L   D   S   D   G   S   F   F   L   Y   S          409
1260  AACAACTACAAGACCACGCCTCCCGTGCTGGACTCCGACGGCTCCTTCTTCCTCTACAGC          1319

410   K   L   T   V   D   K   S   R   W   Q   Q   G   N   V   F   S   C   S   V   M          429
1320  AAGCTCACCGTGGACAAGAGCAGGTGGCAGCAGGGGAACGTCTTCTCATGCTCCGTGATG          1379

430   H   E   A   L   H   N   H   Y   T   Q   K   S   L   S   L   S   P   G   K   Trm        448
1380  CATGAGGCTCTGCACAACCACTACACGCAGAAGAGCCTCTCCCTGTCTCCGGGTAAATGA          1439

HindIII
1440  GTGCCGACGGCCCCCAAGCTT                                                                   1458
```

Fig. 7

```
                                                    M  G  W  S  C  I  I  L      -12
         HindIII
    1    AAGCTTACAGTTACTGAGCACACAGGACCTTCACCATGGGATGGAGCTGTATCATCCTC              59

F  L  V  A  T  A  T  G  V  H  S  Q  V  Q  L  Q  E  S  G  P              9
   60    TTCTTGGTAGCAACAGCTACACAGGTGTCCACTCCCAGGTCCAGCTGCAGGAGAGCGGGTCCA          119

G  L  V  R  P  S  Q  T  L  S  L  T  C  T  V  S  G  F  T  F              29
  120    GGTCTTGTGAGACCTAGCCAGACCCTGAGCCTGACCTGCACCGTGTCTGGCTTCACCTTC            179
                                                    CDR 1
         S │ N  Y  G  M  A │ W  V  R  Q  P  P  P  G  R  G  L  E  W  I  G          49
  180    AGCAACTATGGCATGGCATGGGTCCGTGAGACAGCCACCTGGACGAGGTCTTGAGTGGATTGGA        239
                                              CDR 2
         T │ I  S  H  D  G  S  D  T  Y  F  R  D  S  V  K │ G  R  V  T            69
  240    ACCATTAGTCATGATGGTAGTGACACTTACTTTCGAGACTCTGTGAAGGGGAGAGTGACA            299
```

Fig. 7A

```
 70   M   L   V   D   T   S   K   N   Q   F   S   L   R   L   S   S   V   T   A   A      89
300  ATGCTGGTAGACACCAGCAAGAACCAGTTCAGCCTGAGACTCAGCAGCGTGACAGCCGCC              359

CDR 3
 90   D   T   A   V   Y   Y   C   A   R  |Q   G   T   I   A   G   I   R   H | W   G     109
360  GACACCGCGGTCTATTATTGTGCAAGACAAGGCACTATAGCTGGTATACGTCACTGGGGT              419

110   Q   G   S   L   V   T   V   S   S   A   S   T   K   G   P   S   V   F   P   L     129
420  CAAGGCAGCCTCGTCACAGTCTCCTCAGCCTCCACCAAGGGCCCATCGGTCTTCCCCCTG              479

130   A   P   S   S   K   S   T   S   G   G   T   A   A   L   G   C   L   V   K   D     149
480  GCACCCTCCTCCAAGAGCACCTCTGGGGGCACAGCGGCCCTGGGCTGCCTGGTCAAGGAC              539

150   Y   F   P   E   P   V   T   V   S   W   N   S   G   A   L   T   S   G   V   H     169
540  TACTTCCCCGAACCGGTGACGGTGTCGTGGAACTCAGGCGCCCTGACCAGCGGCGTGCAC              599
```

Fig. 7B

| | | | |
|---|---|---|---|
| 170 | T F P A V L Q S S G L Y S L S S V V T V | 189 | |
| 600 | ACCTTCCCGGCTGTCCTACAGTCCTCAGGACTCTACTCCCTCAGCAGCGTGGTGACCGTG | 659 | |
| 190 | P S S S L G T Q T Y I C N V N H K P S N | 209 | |
| 660 | CCCTCCAGCAGCTTGGGCACCCAGACCTACATCTGCAACGTGAATCACAAGCCCAGCAAC | 719 | |
| 210 | T K V D K K V E P K S C D K T H T C P P | 229 | |
| 720 | ACCAAGGTGGACAAGAAAGTTGAGCCCAAATCTTGTGACAAAACTCACACATGCCCACCG | 779 | |
| 230 | C P A P E L L G G P S V F L F P P K P K | 249 | |
| 780 | TGCCCAGCACCTGAACTCCTGGGGGGACCGTCAGTCTTCCTCTTCCCCCCAAAACCCAAG | 839 | |
| 250 | D T L M I S R T P E V T C V V V D V S H | 269 | |
| 840 | GACACCCTCATGATCTCCCGGACCCCTGAGGTCACATGCGTGGTGGTGGACGTGAGCCAC | 899 | |

Fig. 7C

```
270  E  D  P  E  V  K  F  N  W  Y  V  D  G  V  E  V  H  N  A  K    289
900  GAAGACCCTGAGGTCAAGTTCAACTGGTACGTGGACGGCGTGGAGGTGCATAATGCCAAG    959

290  T  K  P  R  E  E  Q  Y  N  S  T  Y  R  V  V  S  V  L  T  V    309
960  ACAAAGCCGCGGGAGGAGCAGTACAACAGCACGTACCGTGTGGTCAGCGTCCTCACCGTC   1019

310  L  H  Q  D  W  L  N  G  K  E  Y  K  C  K  V  S  N  K  A  L    329
1020 CTGCACCAGGACTGGCTGAATGGCAAGGAGTACAAGTGCAAGGTCTCCAACAAAGCCCTC   1079

330  P  A  P  I  E  K  T  I  S  K  A  K  G  Q  P  R  E  P  Q  V    349
1080 CCAGCCCCCATCGAGAAAACCATCTCCAAAGCCAAAGGGCAGCCCCGAGAACCACAGGTG   1139

350  Y  T  L  P  P  S  R  D  E  L  T  K  N  Q  V  S  L  T  C  L    369
1140 TACACCCTGCCCCCATCCCGGGATGAGCTGACCAAGAACCAGGTCAGCCTGACCTGCCTG   1199
```

Fig. 7D

```
370   V   K   G   F   Y   P   S   D   I   A   V   E   W   E   S   N   G   Q   P   E    389
1200  GTCAAAGGCTTCTATCCCAGGACATCGCCGTGGAGTGGGAGAGCAATGGGCAGCCGGAG    1259

390   N   N   Y   K   T   T   P   P   V   L   D   S   D   G   S   F   F   L   Y   S    409
1260  AACAACTACAAGACCACGCCTCCCGTGCTGGACTCCGACGGCTCCTTCTTCCTCTACAGC   1319

410   K   L   T   V   D   K   S   R   W   Q   Q   G   N   V   F   S   C   S   V   M    429
1320  AAGCTCACCGTGGACAAGAGCAGGTGGCAGCAGGGGAACGTCTTCTCATGCTCCGTGATG   1379

430   H   E   A   L   H   N   H   Y   T   Q   K   S   L   S   L   S   P   G   K   Trm  448
1380  CATGAGGCTCTGCACAACCACTACACGCAGAAGAGCCTCTCCCTGTCTCCGGGTAAATGA   1439

HindIII
1440  GTGCCGACGGCCCCAAGCTT   1458
```

Fig. 8

```
  1                                                                          13
  Q  V  Q  L  V  E  S  G  G  G  V  V  Q 14                                                                          33
                                                              ┌─CDR 1──┐
  P  G  R  S  L  R  L  S  C  S  S  S  G  F  I  F  S │ S  Y  A │

34                                                                          53
                                                                 ┌─CDR 2
  M │ Y │ W  V  R  Q  A  P  G  K  L  E  W  V  A    │ I  I  W  D 54                                                                          73
  ──────────────────────────────┐
  D  G  S  D  Q  H  Y  A  D  S  V  K  G │ R  F  T  I  S  R  D 74                                                                          93
  N  S  K  N  T  L  F  L  Q  M  D  S  L  R  P  E  D  T  G  V 94                                                                         113
                  ┌─────────────────── CDR 3 ─────────────────┐
  Y  F  C  A  R │ D  G  G  H  G  F  C  S  S  A  S  C  F  G  P 114                                                          126
  │ D │ Y  W  G  Q  G  T  P  V  T  V  S  S
```

Fig. 9

```
        HindIII
1       AAGCTTATGAATATGCAAATCCTCTGAATCTACATGGTAAATATAGGTTTGTCTATACC          59

60      ACAAACAGAAAAACATGAGATCACAGTTCTCTCTACAGTTACTCAGCACACAGGACCTCA        119

-19          M  G  W  S  C  I  I  L  F  L  V  A  T  A  T                   -5
120     CCATGGGATGGAGCTGTATCATCCCTCTTCTTGGTAGCACACAGCTACAGG                 179

180     CAGTAGCAGGCTTGAGCTCTGGACATATATATGGGTGACAATGACATCCACTTTGCCTTT        239

-4             G  V  H  S  Q  V  Q  L  V  E  S  G  G  G  V  V  Q           13
240     CTCTCCACAGGTGTCCACTCCCAGGTCCAACTGGTGGAGTCTGGGGGAGGCGTGGTGCAG        299

CDR1
14       P  G  R  S  L  R  L  S  C  S  S  S  G  F  I  F  S  N  Y  G        33
300     CCTGGAAGGTCCCTGAGACTCTCCTGTTCCTCTTCTGGATTCATCTTCAGTAACTATGGC        359

CDR2
34        M  A  W  V  R  Q  A  P  G  K  G  L  E  W  V  A  T  I  S  H       53
360     ATGGCCTGGGTCCGCCAGGCTCCAGGGAAGGGGCTGGAGTGGGTCGCAACCATTAGTCAT        419
```

Fig. 9A

```
 54   D  G  S  D  T  Y  F  R  D  S  V  K  G │R  F  T  I  S  R  D │    73
420   GATGGTAGTGACACTTACTTTCGAGACTCCGTGAAGGGCCGATTCACTATCTCCAGAGAT    479

74   N  S  K  N  T  L  F  L  Q  M  D  S  L  R  P  E  D  T  G  V     93
480   AATAGCAAAAACACCCTATTCCTGCAAATGGACAGTCTGAGGCCCGAGGACACGGGCGTG    539
                                         CDR 3
 94   Y  F  C  A  R │Q  G  T  I  A  G  I  R  H │W  G  Q  G  T  P    113
540   TATTTCTGTGCAAGACAAGGGACTATAGCAGGTATACGTCACTGGGGCCAAGGGACCCCC    599

114   V  T  V  S  S                                                 118
600   GTCACCGTCTCCTCAGGTGAGTCCCTTACAACCTCTCTCTTCTATTCAGCTTAAATAGATT    659

660   TTACTGCATTGTTGGGGGAAATGTGTATCTGAATTTCAGTTCATGAAGGACTAGG         719

720   GACACCTTGGAGTCAGAAAGGGTCATTGGGAGCCCGATGCAGACAGACATCCTC          779
                                                  BamHI
780   AGCTCCCAGACTTCATGGCCAGAGATTTATAGGGATCC                         817
```

Fig. 10

```
                                            M  G  W  S  C  I  I  L  F    -11
       HindIII
   1   AAGCTTTACAGTTACTTCAGCACACAGGACCCTCACCATGGAGCTGTATCATCCTCT          60

L  V  A  T  A  T                                                  -5
  61   TCTTGGTAGCAACAGTACACAGTAGCAGGCTTGAGTCTGGACATA                      120

G  V  H  S  Q  V                             2
 121   TATATGGGTGACAATGACATCCACTTTGCCTTTCTCTCCACAGGTGTCCACTCCCAGGTC       180

Q  L  V  E  S  G  G  G  V  V  Q  P  G  R  S  L  R  L  S  C        22
 181   CAACTGGTGGAGTCTGGGGGAGGCGTGGTGCAGCCTGGGAGGTCCCTGAGACTCTCCTGT       240

CDR 1
        S  S  S  G  F  I  F  S | N  Y  G  M  A | W  V  R  Q  A  P  G      42
 241   TCCTCCTCTGGATTCATCTTCAGTAACTATGGCATGGCCTGGGTCCGCCAGGCTCCAGGC       300

CDR 2
        K  G  L  E  W  V  A | T  I  S  H  D  G  S  D  T  Y  F  R  D       62
 301   AAGGGGCTGGAGTGGGTCGCAACCATTAGTCATGATGGTAGTGACACTTACTTTCGAGAC       360
```

Fig. 10A

```
 63  S  V  K  G  R  F  T  I  S  R  D  N  S  K  N  T  L  F  L  Q    82
361  TCCGTGAAGGGCCGATTCACTATCTCCAGAGATAATAGCAAAAACACCCTATTCCTGCAA   420

CDR 3
 83  M  D  S  L  R  P  E  D  T  G  V  Y  F  C  A  R  Q  G  T  I   102
421  ATGGACAGTCTGAGGCCCGAGGACACGGGGGTGTATTTCTGTGCAAGACAAGGACTATA    480

103  A  G  I  R  H  W  G  Q  G  T  P  V  T  V  S  S                122
481  GCAGGTATACGTCACTGGGGCCAAGGGACCCCCGTCACCGTCTCCTCAGGTGAGTCCTTA   540

541  CAACCCTCTCTCTTCTATTCAGCTTAAATAGATTTACTGCATTTGTTGGGGGGAAATGT    600

601  GTGTATCTGAATTTCAGGTCATGAAGGACTAGGGACACCTTGGGAGTCAGAAAGGGTCAT   660

661  TGGGAGCCCGGGCTGATGCAGACAGACATCCTCAGCTCCCAGACTTCATGGCCAGAGATT   720

BamHI
721  TATAGGGATCC                                                    731
```

Fig. 11

```
        HindIII
  1     AAGCTTATGAATATGCAAATCCCTCTGAATCTACATGGTAAATATAGGTTTGTCTATACC    59

60     ACAAACAGAAAAACATGAGATCACAGTTCTCTCTACAGTTACTCAGCACACAGGACCTCA   119

M  G  W  S  C  I  I  L  F  L  V  A  T  A  T          -5
120     CCATGGGATGGAGCTGTATCATCCTCTTCTTGGTAGCAACAGGTACAGGTAAGGGGCTCA   179

180     CAGTAGCAGGCTTGAGGTCTGGACATATATGGGTGACAATGACATCCACTTTGCCTTT      239

G  V  H  S  Q  V  Q  L  V  E  S  G  G  G  V  V  Q     13
240     CTCTCCACAGGTGTCCACTCCCAGGTCCAACTGGTGGAGTCTGGTGGAGGTGGTGTGCAG   299

CDR 1
         P  G  R  S  L  R  L  S  C  S  S  S  G  F  I  F  S  N  Y  G     33
300     CCTGGAAGGTCCCTGAGACTCTCCTGTTCCTCTCTGGATTCATCTTCAGTAACTATGGC   359

CDR 2
         L  E  W  V  A  T  I  S  H                                       53
                       M  A  W  V  R  Q  A  P  G  K  G
360     ATGGCCTGGGTCCGCCAGGCTCCAGGCAAGGGGCTGGAGTGGGTCGCAACCATTAGTCAT   419
```

Fig. 11A

```
 54    D  G  S  D  T  Y  F  R  D  S  V  K  G │R  F  T  I  S  R  D    73
420   GATGGTAGTGACACTTACTTCCGAGACTCCGTGAAGGGCCGATTCACTATCTCCAGAGAT   479

74    N  S  K  N  T  L  F  L  Q  M  D  S  L  R  P  E  D  T  G  V    93
480   AATAGCAAAAACACCCTATTCCTGCAAATGGACAGTCTGAGGCCCGAGGACACGGGCGTG   539
                                                            CDR 3
 94    Y  F  C  A  R │Q  G  T  I  A  G  I  R  H│ W  G  Q  G  T  T   113
540   TATTTCTGTGCAAGACAAGGGACTATAGCAGGTATACGTCACTGGGGCCAAGGGACCACG   599

114    V  T  V  S  S                                                118
600   GTCACCGTCTCCTCAGGTGAGTCCTTACAACCTCTCTCTTCTATTCAGCTTAAATAGATT   659

660   TTACTGCATTGTTGTGGGGGGAAATGTGTATCTGAATTTCAGGTCATGAAGGACTAGG    719

720   GACACCTTGGAGTCAGAAAGGGTCATTGGGAGCCCGGGCTGATGCAGACAGACATCCTC    779
                                                         BamHI
780   AGCTCCCAGACTTCATGGCCCAGAGATTTATAGGGATCC                        817
```

Fig. 12

```
                                  M  G  W  S  C  I  I  L  F     -11
     HindIII
-19  AAGCTTTACAGTTACTCAGCACACAGGACCTCACCATGGGATGGAGCTGTATCATCCTCT   60
 1

L  V  A  T  A  T                                             -5
-10  TCTTGGTAGCAACAGCTACACAGGTAAGGGGCTCACAGGCTTGAGGTCTGGACATA       120
 61

G  V  H  S  Q  V    2
 -4  TATATGGGTGACAATGACATCCACTTTGCCTTTCTCCTCCACAGTGTCCACTCCCAGGTC  180
121

Q  L  V  E  S  G  G  G  V  V  Q  P  G  R  S  L  R  L  S  C   22
  3  CAACTGGTGGAGTCTGGGGGAGGCGTGGTGCAGCCTGGGAGGTCCCTGAGACTCTCCTGT  240
181
                                              CDR 1
     S  S  S  G  F  I  F  S │N  Y  G  M  A│ W  V  R  Q  A  P  G   42
 23  TCCTCCTCTGGATTCATCTTCAGTAACTATGGCATGGCCTGGGTCCGCCAGGCTCCAGGC  300
241
                                                         CDR 2
     K  G  L  E  W  V  A │T  I  S  H  D  G  S  D  T  Y  F  R  D   62
 43  AAGGGGCTGGAGTGGGTCGCAACCATTAGTCATGATGGTAGTGACACTTACTTCGAGAC   360
301

S  V  K  G│ R  F  T  I  S  R  D  N  S  K  N  T  L  F  L  Q   82
 63  TCCGTGAAGGGCCGATTCACTATCTCCAGAGATAATAGCAAAAACACCCTATTCCTGCAA  420
361
```

Fig. 12A

```
 83   M  D  S  L  R  P  E  D  T  G  V  Y  F  C  A  R                             CDR 3
                                                       Q  G  T  I                        102
421   ATGGACAGTCTGAGGCCCGAGGACACGGGCGTGTATTTCTGTGCAAGACAAGGGACTATA                         480

103   A  G  I  R  H  W  G  Q  G  T  T  V  T  V  S  S                                     122
481   GCAGGTATACGTCACTGGGGCCAAGGGACCACGGTCACCGTCTCCTCAGGTGAGTCCTTA                        540

541   CAACCTCTCCTTCTATTCAGCTTAAATAGATTTACTGCATTTGTTGGGGGAAATGT                             600

601   GTGTATCTGAATTTCAGGTCATGAAGGACTAGGGACACCTTGGGAGTCAGAAAGGGTCAT                         660

661   TGGGAGCCCGGGGCTGATGCAGACACAGACATCCCTCAGCTCCCAGACTTCATGGCCAGAGATT                     720

BamHI
721   TATAGGGATCC                                                                        731
```

ALTERED ANTIBODIES AND THEIR PREPARATION

This application is a 371 of PCT/GB91/01578, filed Sep. 16, 1991.

The present invention relates to altered antibodies and their preparation. The invention is typically applicable to the production of humanised antibodies.

Antibodies typically comprise two heavy chains linked together by disulphide bonds and two light chains. Each light chain is linked to a respective heavy chain by disulphide bonds. Each heavy chain has at one end a variable domain followed by a number of constant domains. Each light chain has a variable domain at one end and a constant domain at its other end. The light chain variable domain is aligned with the variable domain of the heavy chain. The light chain constant domain is aligned with the first constant domain of the heavy chain. The constant domains in the light and heavy chains are not involved directly in binding the antibody to antigen.

The variable domains of each pair of light and heavy chains form the antigen binding site. The domains on the light and heavy chains have the same general structure and each domain comprises a framework of four regions, whose sequences are relatively conserved, connected by three complementarity determining regions (CDRs). The four framework regions largely adopt a beta-sheet conformation and the CDRs form loops connecting, and in some cases forming part of, the beta-sheet structure. The CDRs are held in close proximity by the framework regions and, with the CDRs from the other domain, contribute to the formation of the antigen binding site.

The preparation of an altered antibody in which the CDRs are derived from a different species than the framework of the antibody's variable domains is disclosed in EP-A-0239400. The CDRs may be derived from a rat or mouse monoclonal antibody. The framework of the variable domains, and the constant domains, of the altered antibody may be derived from a human antibody. Such a humanised antibody elicits a negligible immune response when administered to a human compared to the immune response mounted by a human against a rat or mouse antibody. Humanised CAMPATH-1 antibody is disclosed in EP-A-0328404.

We have now devised a new way of preparing an altered antibody. In contrast to previous proposals, this involves altering the framework of a variable domain rather than the CDRs. This approach has the advantages that it does not require a pre-existing cDNA encoding, for example, a human framework to which to reshape and that it is technically easier than prior methodologies.

Accordingly, the present invention provides a process for the preparation of an antibody chain in which the CDRs of the variable domain of the antibody chain are derived from a first mammalian species and the framework of the variable domain and, if present, the or each constant domain of the antibody chain are derived from a second different mammalian species, which process comprises:

(i) mutating the framework-encoding regions of DNA encoding a variable domain of an antibody chain of the said first species such that the mutated framework-encoding regions encode the said framework derived from the said second species; and (ii) expressing the said antibody chain utilising the mutated DNA from step (i).

A variable domain of either or both chains of an antibody can therefore be altered by:

(a) determining the nucleotide and predicted amino acid sequence of a variable domain of a selected antibody chain of the said first species;

(b) determining the antibody framework to which the framework of the said variable domain is to be altered;

(c) mutating the framework-encoding regions of DNA encoding the said variable domain such that the mutated framework-encoding regions encode the framework determined upon in step (b);

(d) linking the mutated DNA obtained in step (c) to DNA encoding a constant domain of the said second species and cloning the DNA into an expression vector; and (e) introducing the expression vector into a compatible host cell and culturing the host cell under such conditions that antibody chain is expressed.

The antibody chain may be co-expressed with a complementary antibody chain. At least the framework of the variable domain and the or each constant domain of the complementary chain generally are derived from the said second species also. A light chain and a heavy chain may be co-expressed. Either or both chains may have been prepared by the process of the invention. Preferably the CDRs of both chains are derived from the same selected antibody. An antibody comprising both expressed chains can be recovered.

The antibody preferably has the structure of a natural antibody or a fragment thereof. The antibody may therefore comprise a complete antibody, a $(Fab')_2$ fragment, a Fab fragment, a light chain dimer or a heavy chain. The antibody may be an IgG such as an IgG1, IgG2, IgG3 or IgG4 IgM, IgA, IgE or IgD. Alternatively, the antibody may be a chimaeric antibody of the type described in WO 86/01533.

A chimaeric antibody according to WO 86/01533 comprises an antigen binding region and a non-immunoglobulin region. The antigen binding region is an antibody light chain variable domain or heavy chain variable domain. Typically, the chimaeric antibody comprises both light and heavy chain variable domains. The non-immunoglobulin region is fused at its C-terminus to the antigen binding region. The non-immunoglobulin region is typically a non-immunoglobulin protein and may be an enzyme region, a region derived from a protein having known binding specificity, from a protein toxin or indeed from any protein expressed by a gene. The two regions of the chimaeric antibody may be connected via a cleavable linker sequence.

The invention is preferably employed to humanise an antibody, typically a monoclonal antibody and, for example, a rat or mouse antibody. The framework and constant domains of the resulting antibody are therefore human framework and constant domains whilst the CDRs of the light and/or heavy chain of the antibody are rat or mouse CDRs. Preferably all CDRs are rat or mouse CDRs. The antibody may be a human IgG such as IgG1, IgG2, IgG3, IgG4; IgM; IgA; IgE or IgD carrying rat or mouse CDRs.

The process of the invention is carried out in such a way that the resulting antibody retains the antigen binding capability of the antibody from which it is derived. An antibody is reshaped according to the invention by mutating the framework-encoding regions of DNA coding for the variable domains of the antibody. This antibody and the reshaped antibody should both be capable of binding to the same antigen.

The starting antibody is typically an antibody of a selected specificity. In order to ensure that this specificity is retained, the variable domain framework of the antibody is preferably reshaped to about the closest variable domain framework of an antibody of another species. By "about the closest" is meant about the most homologous in terms of amino acid sequences. Preferably there is a homology of at least 50% between the two variable domains.

There are four general steps to reshape a monoclonal antibody. These are:
(1) determining the nucleotide and predicted amino acid sequence of the starting antibody light and heavy chain variable domains;
(2) designing the reshaped antibody, i.e. deciding which antibody framework region to use during the reshaping process;
(3) the actual reshaping methodologies/techniques; and
(4) the transfection and expression of the reshaped antibody.

These four steps are explained below in the context of humanising an antibody. However, they may equally well be applied when reshaping to an antibody of a non-human species.

Step 1: Determining the Nucleotide and Predicted Amino Acid Sequence of the Antibody Light and Heavy Chain Variable Domains To reshape an antibody only the amino acid sequence of antibody's heavy and light chain variable domains needs to be known. The sequence of the constant domains is irrelevant because these do not contribute to the reshaping strategy. The simplest method of determining an antibody's variable domain amino acid sequence is from cloned cDNA encoding the heavy and light chain variable domain.

There are two general methods for cloning a given antibody's heavy and light chain variable domain cDNAs: (1) via a conventional cDNA library, or (2) via the polymerase chain reaction (PCR). Both of these methods are widely known. Given the nucleotide sequence of the cDNAs, it is a simple matter to translate this information into the predicted amino acid sequence of the antibody variable domains.

Step 2: Designing the Reshaped Antibody

There are several factors to consider in deciding which human antibody sequence to use during the reshaping. The reshaping of light and heavy chains are considered independently of one another, but the reasoning is basically similar for each.

This selection process is based on the following rationale: A given antibody's antigen specificity and affinity is primarily determined by the amino acid sequence of the variable region CDRs. Variable domain framework residues have little or no direct contribution. The primary function of the framework regions is to hold the CDRs in their proper spacial orientation to recognize antigen. Thus the substitution of rodent CDRs into a human variable domain framework is most likely to result in retention of their correct spacial orientation if the human variable domain is highly homologous to the rodent variable domain from which they originated. A human variable domain should preferably be chosen therefore that is highly homologous to the rodent variable domain(s).

A suitable human antibody variable domain sequence can be selected as follows:
1. Using a computer program, search all available protein (and DNA) databases for those human antibody variable domain sequences that are most homologous to the rodent antibody variable domains. This can be easily accomplished with a program called FASTA but other suitable programs are available. The output of a suitable program is a list of sequences most homologous to the rodent antibody, the percent homology to each sequence, and an alignment of each sequence to the rodent sequence. This is done independently for both the heavy and light chain variable domain sequences. The above analyses are more easily accomplished if customized sub-databases are first created that only include human immunoglobulin sequences. This has two benefits. First, the actual computational time is greatly reduced because analyses are restricted to only those sequences of interest rather than all the sequences in the databases. The second benefit is that, by restricting analyses to only human immunoglobulin sequences, the output will not be cluttered by the presence of rodent immunoglobulin sequences. There are far more rodent immunoglobulin sequences in databases than there are human.
2. List the human antibody variable domain sequences that have the most overall homology to the rodent antibody variable domain (from above). Do not make a distinction between homology within the framework regions and CDRs. Consider the overall homology.
3. Eliminate from consideration those human sequences that have CDRs that are a different length than those of the rodent CDRs. This rule-does not apply to CDR 3, because the length of this CDR is normally quite variable. Also, there are sometimes no or very few human sequences that have the same CDR lengths as that of the rodent antibody. If this is the case, this rule can be loosened, and human sequences with one or more differences in CDR length can be allowed.
4. From the remaining human variable domains, the one is selected that is most homologous to that of the rodent.
5. The actual reshaped antibody (the end result) should contain CDRs derived from the rodent antibody and a variable domain framework from the human antibody chosen above.

Step 3: The Actual Reshaping Methodologies/techniques

A cDNA encoding the desired reshaped antibody is preferably made beginning with the rodent cDNA from which the rodent antibody variable domain sequence(s) was originally determined. The rodent variable domain amino acid sequence is compared to that of the chosen human antibody variable domain sequence. The residues in the rodent variable domain framework are marked that need to be changed to the corresponding residue in the human to make the rodent framework identical to that of the human framework. There may also be residues that need adding to or deleting from the rodent framework sequence to make it identical to that of the human.

Oligonucleotides are synthesised that can be used to mutagenize the rodent variable domain framework to contain the desired residues. Those oligonucleotides can be of any convenient size. One is normally only limited in length by the capabilities of the particular synthesizer one has available. The method of oligonucleotide-directed in vitro mutagenesis is well known.

The advantages of this method of reshaping as opposed to splicing CDRs into a human framework are that (1) this method does not require a pre-existing cDNA encoding the human framework to which to reshape and (2) splicing CDRs is technically more difficult because there is usually a large region of poor homology between the mutagenic oligonucleotide and the human antibody variable domain. This is not so much a problem with the method of splicing human framework residues onto a rodent variable domain because there is no need for a pre-existing cDNA encoding the human variable domain. The method starts instead with the rodent cDNA sequence. Also, splicing framework regions is technically easier because there is a high degree of homology between the mutagenic oligonucleotide and the rodent variable domain framework. This is true because a human antibody variable domain framework has been selected that is most homologous to that of the rodent.

The advantage of the present method of reshaping as opposed to synthesizing the entire reshaped version from scratch is that it is technically easier. Synthesizing a reshaped variable domain from scratch requires several more oligonucleotides, several days more work, and technical difficulties are more likely to arise.

Step 4: The Transfection and Expression of the Reshaped Antibody

Following the mutagenesis reactions to reshape the antibody, the cDNAs are linked to the appropriate DNA encoding light or heavy chain constant region, cloned into an expression vector, and transfected into mammalian cells. These steps can be carried out in routine fashion. A reshaped antibody may therefore be prepared by a process comprising:

a) preparing a first replicable expression vector including a suitable promoter operably linked to a DNA sequence which encodes at least a variable domain of an Ig heavy or light chain, the variable domain comprising framework regions from a first antibody and CDRs comprising at least parts of the CDRs from a second antibody of different specificity;

b) if necessary, preparing a second replicable expression vector including a suitable promoter operably linked to a DNA sequence which encodes at least the variable domain of a complementary Ig light or heavy chain respectively;

c) transforming a cell line with the first or both prepared vectors; and d) culturing said transformed cell line to produce said altered antibody.

Preferably the DNA sequence in step a) encodes both the variable domain and the or each constant domain of the antibody chain, the or each constant domain being derived from the first antibody. The antibody can be recovered and purified. The cell line which is transformed to produce the altered antibody may be a Chinese Hamster Ovary (CHO) cell line or an immortalised mammalian cell line, which is advantageously of lymphoid origin, such as a myeloma, hybridoma, trioma or quadroma cell line. The cell line may also comprise a normal lymphoid cell, such as a B-cell, which has been immortalised by transformation with a virus, such as the Epstein-Barr virus. Most preferably, the immortalised cell line is a myeloma cell line or a derivative thereof.

Although the cell line used to produce the altered antibody is preferably a mammalian cell line, any other suitable cell line, such as a bacterial cell line or a yeast cell line, may alternatively be used. In particular, it is envisaged that *E. coli*—derived bacterial strains could be used.

It is known that some immortalised lymphoid cell lines, such as myeloma cell lines, in their normal state secrete isolated Ig light or heavy chains. If such a cell line is transformed with the vector prepared in step (a) it will not be necessary to carry out step (b) of the process, provided that the normally secreted chain is complementary to the variable domain of the Ig chain encoded by the vector prepared in step (a).

However, where the immortalised cell line does not secrete or does not secrete a complementary chain, it will be necessary to carry out step (b). This step may be carried out by further manipulating the vector produced in step (a) so that this vector encodes not only the variable domain of an altered antibody light or heavy chain, but also the complementary variable domain.

Alternatively, step (b) is carried out by preparing a second vector which is used to transform the immortalised cell line. This alternative leads to easier construct preparation, but may be less preferred than the first alternative in that it may not lead to as efficient production of antibody.

In the case where the immortalised cell line secretes a complementary light or heavy chain, the transformed cell line may be produced for example by transforming a suitable bacterial cell with the vector and then fusing the bacterial cell with the immortalised cell Line by spheroplast fusion. Alternatively, the DNA may be directly introduced into the immortalised cell line by electroporation or other suitable method.

An antibody is consequently produced in which CDRs of a variable domain of an antibody chain are homologous with the corresponding CDRs of an antibody of a first mammalian species and in which the framework of the variable domain and the constant domains of the antibody are homologous with the corresponding framework and constant domains of an antibody of a second, different, mammalian species. Typically, all three CDRs of the variable domain of a light or heavy chain are derived from the first species.

The present process has been applied to obtain an antibody against human CD4 antigen. Accordingly, the invention also provides an antibody which is capable of binding to human CD4 antigen, in which the CDRs of the light chain of the antibody have the amino acid sequences:

CDR1: LASEDIYSDLA (SEQ ID NO:13)

CDR2: NTDTLQN (SEQ ID NO:14)

CDR3: QQYNNYPWT (SEQ ID NO:15), in which the CDRs of the heavy chain of the antibody have the amino acid sequences:

CDR1: NYGMA (SEQ ID NO:16)

CDR2: TISHDGSDTYFRDSVKG (SEQ ID NO:17)

CDR3: QGTIAGIRH (SEQ ID NO:18), and in which the framework of the variable domain and, if present, the or each constant domain of each chain are derived from a mammalian non-rat species.

The antibody preferably has the structure of a natural antibody or a fragment thereof. The antibody may therefore comprise a complete antibody, a (Fab')$_2$ fragment, a Fab fragment, a light chain dimer or a heavy chain.

The antibody may be an IgG such as IgG1, IgG2, IgG3 or IgG4 IgM, IgA, IgE or IgD. Alternatively, the antibody may be a chimaeric antibody of the type described in WO 86/01533.

A chimaeric antibody according to WO 86/01533 comprises an antigen binding region and a non-immunoglobulin region. The antigen binding region is an antibody light chain variable domain or heavy chain variable domain. Typically the chimaeric antibody comprises both light and heavy chain variable domains. The non-immunoglobulin region is fused at its C-terminus to the antigen binding region. The non-immunoglobulin region is typically a non-immunoglobulin protein and may be an enzyme region, a region derived from a protein having known binding specificity, from a protein toxin or indeed from any protein expressed by a gene. The two regions of the chimaeric antibody may be connected via a cleavable linker sequence.

The invention is preferably employed to humanise a CD4 antibody such as a rat or mouse CD4 antibody. The framework and the constant domains of the resulting antibody are therefore human framework and constant domains whilst the CDRs of the light and/or heavy chain of the antibody are rat or mouse CDRs. Preferably all CDRs are rat or mouse CDRs. The antibody may be a human IgG such as IgG1, IgG2, IgG3, IgG4; IgM; IgA; IgE or IgD carrying rat or mouse CDRs.

Preferably the framework of the antibody heavy chain is homologous to the corresponding framework of the human antibody KOL (Schmidt et al, Hoppe-Seyler's Z. Physiol. Chem., 364 713–747, 1983). The sixth residue of framework 4 in this case is suitably Thr or Pro, preferably Thr. This residue is the 121st residue in the KOL antibody heavy chain variable region (Schmidt et al, 1983), and is identified as residue 108 by Kabat (Kabat et al, "Sequences of proteins of immunological interest", US Dept of Health and Human Services, US Government Printing Office, 1987). Alternatively, the framework of the antibody heavy chain is homologous to the corresponding framework of the human antibody NEW (Saul et al, J. Biol. Chem. 2: 585–597, 1978). The final residue of framework 1 in this case is suitably Ser or Thr, preferably Ser. This residue is at position 30 (Kabat et al, 1987). Preferably the framework of the antibody light chain is homologous to the variable domain framework of the protein REI (Epp et al, Eur. J. Biochem., 45, 513–524, 1974).

The framework regions of one or both chains of a CD4 antibody can be reshaped by the present process. Alternatively, one or both chains of a CD4 antibody may be reshaped by the procedure described in EP-A-0239400. The procedure of EP-A-0239400 involves replacing CDRs rather than the replacement of frameworks. The CDRs are grafted onto a framework derived from a mammalian non-rat species, typically a human. This may be achieved by oligonucleotide-directed in vitro mutagenesis of the CDR-encoding regions of an antibody chain, light or heavy, from a mammalian non-rat species. The oligonucleotides in such an instance are selected so that the resulting CDR-grafted antibody has the light chain CDRs 1 to 3 and the heavy chain CDRs 1 to 3 shown above.

The reshaped CD4 antibody can be used to induce tolerance to an antigen. It can be used to alleviate autoimmune diseases such as rheumatoid arthritis. It can be used to prevent graft rejection. Tolerance to a graft such as an organ graft or a bone marrow transplantation can be achieved. Also, the reshaped CD4 antibody might be used to alleviate allergies. Tolerance to allergens could be achieved.

The CD4 antibody may be depleting or non-depleting. A depleting antibody is an antibody which depletes more than 50%, for example from 90 to 99%, of target cells in vivo. A non-depleting antibody depletes fewer than 50%, for example, from 10 to 25% and preferably less than 10% of target cells in vivo. A CD4 antibody may be administered alone or may be co-administered with a non-depleting or depleting CD8 antibody. The CD4 antibody, depleting or non-depleting, and CD8 monoclonal antibody, depleting or non-depleting, may be administered sequentially in any order or may be administered simultaneously. An additional antibody, drug or protein may be administered before, during or after administration of the antibodies.

A CD4 antibody and, indeed, a CD8 antibody as appropriate are given parenterally, for example intravenously. The antibody may be administered by injection or by infusion. For this purpose the antibody is formulated in a pharmaceutical composition further comprising a pharmaceutically acceptable carrier or diluent. Any appropriate carrier or diluent may be employed, for example phosphate-buffered saline solution.

The amount of non-depleting or depleting CD4 and, if desired, CD8 antibody administered to a patient depends upon a variety of factors including the age and weight of a patient, the condition which is being treated and the antigen(s) to which it is desired to induce tolerance. In a model mouse system from 1 μg to 2 mg, preferably from 400 μg to 1 mg, of a mAb is administered at any one time. In humans from 3 to 500 mg, for example from 5 to 200 mg, of antibody may be administered at any one time. Many such doses may be given over a period of several weeks, typically 3 weeks.

A foreign antigen(s) to which it is desired to induce tolerance can be administered to a host before, during, or after a course of CD4 antibody (depleting or non-depleting) and/or CDs antibody (depleting or non-depleting). Typically, however, the antigen(s) is administered one week after commencement of antibody administration, and is terminated three weeks before the last antibody administration.

Tolerance can therefore be induced to an antigen in a host by administering non-depleting or depleting CD4 and CD8 mAbs and, under cover of the mAbs, the antigen. A patient may be operated on surgically under cover of the non-depleting or depleting CD4 and CD8 mAbs to be given a tissue transplant such as an organ graft or a bone marrow transplant. Also, tolerance may be induced to an antigen already possessed by a subject. Long term specific tolerance can be induced to a self antigen or antigens in order to treat autoimmune disease such as multiple sclerosis or rheumatoid arthritis. The condition of a patient suffering from autoimmune disease can therefore be alleviated.

The following Example illustrates the invention. In the accompanying drawings:

FIGS. 1–1A: shows the nucleotide and predicted amino acid sequence of rat CD4 antibody light chain variable region. The number of the first and last amino acid or nucleotide in each line is indicated in the left and right margins, respectively. Base pairs 1–269 (HindIII-PvuII) and 577–620 ([Bg1II/Bc1I]-BamHI) are part of the vector M13V$_K$PCR3, while base pairs 270–576 are from the PCR product of the CD4 antibody light chain variable region (V$_L$). CDRs (boxes) were identified by comparison to known immunological sequences (Kabat et al, "Sequences of proteins of immunological interest, US Dept of Health and Human Services, US Government Printing Office, 1987). The nucleotide sequence of FIG. 1 corresponds to SEQ ID NO:1.

FIGS. 2–2A: shows the nucleotide and predicted amino acid sequence of the reshaped CAMPATH-1 antibody light chain cDNA. The number of the first and last amino acid or nucleotide in each line is indicated in the left and right margins, respectively. CDRs are identified by boxes. The nucleotide sequence of FIG. 2 corresponds to SEQ ID NO:2.

FIGS. 3–3A: shows the nucleotide and predicted amino acid sequence of the reshaped CD4 antibody light chain cDNA CD4V$_L$REI. The number of the first and last amino acid or nucleotide in each line is indicated in the left and right margins, respectively. CDRs are identified by boxes. The nucleotide sequence of FIG. 3 corresponds to SEQ ID NO:3.

FIGS. 4–4A: shows the nucleotide and predicted amino acid sequence of rat CD4 antibody heavy chain variable region. The number of the first and last amino acid or nucleotide in each line is indicated in the left and right margins, respectively. CDRs are identified by boxes. Base pairs 1–272 (HindIII-PstI) and 603–817 (BstEII-BamHI) are part of the vector M13V$_H$PCR1, while base pairs 273–602 are from the PCR product of the CD4 antibody heavy chain variable region (V$_H$). The nucleotide sequence of FIG. 4 corresponds to SEQ ID NO:4.

FIGS. 5, 5A–D: shows the nucleotide and predicted amino acid sequence of the reshaped CAMPATH-1 antibody heavy chain cDNA. The number of the first and last amino acid or nucleotide in each line is indicated in the left and right margins, respectively. CDRs are identified by boxes. The nucleotide sequence of FIG. 5 corresponds to SEQ ID NO:5.

FIGS. 6, 6A–D: shows the nucleotide and predicted amino acid sequence of the reshaped CD4 antibody heavy chain cDNA CD4V$_H$NEW-Thr$^{30}$. The number of the first and last amino acid or nucleotide in each line is indicated in the left and right margins, respectively. CDRs are identified by boxes. The nucleotide sequence of FIG. 6 corresponds to SEQ ID NO:6.

FIGS. 7, 7A–D: shows the nucleotide and predicted amino acid sequence of the reshaped CD4 antibody heavy chain cDNA CD4V$_H$NEW-Ser$^{30}$. The number of the first and last amino acid or nucleotide in each line is indicated in the left and right margins, respectively. CDRs are identified by boxes. The nucleotide sequence of FIG. 7 corresponds to SEQ ID NO:7.

FIG. 8: shows the heavy chain variable (V) region amino acid sequence of the human myeloma protein KOL. CDRs are identified by boxes. This sequence is taken from the Swiss-Prot protein sequence database. The nucleotide sequence of FIG. 8 corresponds to SEQ ID NO:8.

FIGS. 9–9A: shows the nucleotide and predicted amino acid sequence of the reshaped CD4 antibody heavy chain V region CD4V$_H$KOL-Pro$^{113}$. The number of the first and last amino acid or nucleotide in each line is indicated in the left and right margins, respectively. CDRs are identified by boxes. The nucleotide sequence of FIG. 9 corresponds to SEQ ID NO:9.

FIGS. 10–10A: shows the nucleotide and predicted amino acid sequence of the reshaped CD4 antibody heavy chain V region CD4V$_H$KOL-Pro$^{113}$ without immunoglobulin promoter. The number of the first and last amino acid or nucleotide in each line is indicated in the left and right margins, respectively. CDRs are identified by boxes. The nucleotide sequence of FIG. 10 corresponds to SEQ ID NO:10.

FIGS. 11–11A: shows the nucleotide and predicted amino acid sequence of the reshaped CD4 antibody heavy chain V region CD4V$_H$KOL-Thr$^{113}$. The number of the first and last amino acid or nucleotide in each line is indicated in the left and right margins, respectively. CDRs are identified by boxes. The nucleotide sequence of FIG. 11 corresponds to SEQ ID NO:11.

FIGS. 12–12A: shows the nucleotide and predicted amino acid sequence of the reshaped CD4 antibody heavy chain V region CD4V$_H$KOL-Thr$^{113}$ without immunoglobulin promoter. The number of the first and last amino acid or nucleotide in each line is indicated in the left and right margins, respectively. CDRs are identified by boxes. The nucleotide sequence of FIG. 12 corresponds to SEQ ID NO:12.

FIG. 13: shows the results of an ELISA that compares the avidity of YNB46.1.8 and CD4V$_H$KOL-Thr$^{113}$ antibodies. The X-axis indicates the concentration ($\mu$g/ml) of YNB46.1.8 (triangles) or CD4V$_H$KOL-Thr$^{113}$ (circles) antibody. The Y-axis indicates the optical density at 492 nanometers.

EXAMPLE

1. Materials and Methods

Isolation of monoclonal antibody. The rat-derived anti-human CD4 antibody, clone YNB46.1.8 (IgG$_{2b}$, kappa light chain serotype), was the result of fusion between a rat splenocyte and the Lou strain rat myeloma cell line Y3-Ag 1.2.3 (Galfre et al, Nature, 277: 131–133, 1979) and was selected by its binding to a rat T cell line NB2-6TG stably transfected with an expression vector containing a complementary DNA (cDNA) encoding the human CD4 antigen (Madden et al, Cell, 42: 93–104, 1985). Antibody was purified by high pressure liquid chromatography (HPLC).

Isolation of Antibody Variable Regions. cDNAs encoding the V$_L$ and V$_H$ regions of the CD4 antibody were isolated by a polymerase chain reaction (PCR)-based method (Orlandi et al, PNAS USA, 86: 3833–3837, 1989) with some modifications. Total RNA was isolated from hybridoma cells by the guanidine thiocyanate method (Chirgwin et al, Biochemistry, 18: 5294, 1979), and poly(A)$^+$ RNA was isolated by passage of total RNA through and elution from an oligo(dT)-cellulose column (Aviv and Leder PNAS USA 69: 1408, 1972). Poly(A)$^+$ RNA was heated at 70° C. for 5 minutes and cooled on ice just prior to use. A 25 $\mu$l first strand synthesis reaction consisted of 5 $\mu$g poly(A)$^+$ RNA, 250 $\mu$M each dNTP, 50 mM Tris.HCl (pH 8.2 at 42° C.), 10 mM MgCl$_2$, 100 mM KCl, 10 mM dithiothreitol, 23 units reverse transcriptase (Anglian Biotec, Colchester, U.K.), 3.5 pmoles of the V$_L$ region-specific oligonucleotide primer V$_K$1FOR [5'-d(GTT AGA TCT CCA GCT TGG TCC C)SEQ ID NO:19] or the V$_H$ region-specific prime V$_H$1FOR-B [5,-d(TGA GGA GAC GGT GAC CGT GGT CCC TTG GCC)SEQ ID NO:20], and incubated for 5 minutes at 20° C. and then 90 minutes at 42° C.

Subsequent 50 $\mu$l PCR amplifications consisted of 5 $\mu$l of the first strand synthesis reaction (unpurified), 500 $\mu$M each dNTP, 67 mM Tris-HCl (pH 8.8 at 25° C.), 17 mM (NH$_4$)$_2$SO$_4$, 10 mM MgCl$_2$, 20 $\mu$g/ml gelatin, 5 units TAQ DNA polymerase (Koch-Light, Haverhill, U.K.), and 25 pmoles (each) of primer V$_K$1FOR and V$_K$1BACK [5'-d(GAC ATT CAG CTG ACC CAG TCT)SEQ ID NO:21] for the V$_L$ region or V$_H$1FOR-B and the mixed primer V$_H$1BACK [5'-d(AG GT(CG) (CA)A(GA) CTG CAG (GC)AG TC(TA) GG)SEQ ID NO:22] for the V$_H$ region. Reactions were overlayed with mineral oil and subjected to 30 cycles of 1.5 minutes at 95° C. (denaturation), 1.5 minutes at 37° C. (V$_L$) or 50° C. (V$_H$; annealing), and 3 minutes at 72° C. (extension) with a Techne PHC-1 programmable cyclic reactor. The final cycle contained a 10 minute extension time.

The samples were frozen at −20° C. and the mineral oil (a viscous liquid at −20° C.) was removed by aspiration. The aqueous phases were thawed, and PCR products were purified by electrophoresis in 2% agarose gels, and then double digested with either PvuII and BglII (V$_L$) or PstI and BstEII (V$_H$) restriction enzymes, and cloned into the PvuII and BclI restriction sites of the vector M13V$_K$PCR3 (for V$_L$ region; Orlandi et al, 1989) or the PstI and BstEII restriction sites of the vector M13V$_H$PCR1 (for V$_H$ region). As described in the results, V$_L$ region clones were first screened by hybridisation to a $^{32}$P-labeled oligonucleotide probe [5'-d(GTT TCA TAA TAT TGG AGA CA)SEQ ID NO:23] for the CDR2 of the Y3-Ag 1.2.3 V$_L$ region. V$_L$ region clones not hybridising to this probe and V$_H$ region clones were sequenced by the dideoxy chain termination method (Sanger et al, PNAS USA 74: 5463, 1977).

Reshaped Light Chain Variable Region and Expression Vector Construct

The reshaped light chain was constructed by oligonucleotide-directed in vitro mutagenesis in an M13 vector by priming with three oligonucleotides simultaneously on a 748 base single-stranded cDNA template encoding the entire $V_L$ and kappa constant ($C_K$) regions of the reshaped CAMPATH-1 antibody (Reichmann et al, Nature 332: 323–327, 1988). The three oligonucleotides [5'-d(AGA GTG ACC ATC ACC TGT CTA GCA AGT GAG GAC ATT TAC AGT GAT TTA GCA TGG TAC CAG CAG AAG CCA)SEQ ID NO:24, 5'-d(CTG CTG ATC TAC AAT ACA GAT ACC TTG CAA AAT GGT GTG CCA AGC AGA TTC)SEQ ID NO:25, 5'-d(ATC GCC ACC TAC TAC TGC CAA CAG TAT AAC AAT TAT CCG TGG ACG TTC GGC CAA GGG ACC)SEQ ID NO:26] were designed to replace each of the three CDRs in the REI-based human antibody $V_L$ region framework that is part of the reshaped CAMPATH-1 antibody $V_L$ region (Reichmann et al, 1988). A clone containing each of the three mutant oligonucleotides was identified by nucleotide sequencing and was subcloned into the HindIII site of the expression vector pHβAPr-1 (Gunning et al, PNAS, 4: 4831–4835, 1987) which also contained a dihydrofolate reductase gene (Ringold et al, J. Mol. Appl. Genet. 1: 165–175, 1981) driven by a truncated SV40 promoter.

Reshaped Heavy Chain Variable Regions Based on the Variable Region Framework of the Human Antibody NEW, and Expression Vector Constructs Two versions of the NEW-based reshaped heavy chain were created, $CD4V_H NEW-Thr^{30}$ and $CD4V_H NEW-Ser^{30}$. The $CD4V_H NEW-Thr^{30}$ version (FIG. 6) encodes a threonine residue at position 30 while the $CD4V_H NEW-Ser^{30}$ version (FIG. 7) encodes a Ser residue at position 30. As a matter of convenience, $CD4V_H NEW-Thr^{30}$ was created first by oligonucleotide-directed in vitro mutagenesis in the vector M13mp18 by priming with three oligonucleotides simultaneously on a 1467 base single-stranded cDNA template (FIG. 5) encoding the entire heavy chain of the reshaped CAMPATH-1 antibody (Reichmann et al, 1988). The three oligonucleotides [5'-d(TCT GGC TTC ACC TTC ACC AAC TAT GGC ATG GCC TGG GTG AGA CAG CCA CCT) SEQ ID NO:27, 5'-d(GGT CTT GAG TGG ATT GGA ACC ATT AGT CAT GAT GGT AGT GAC ACT TAC TTT CGA GAC TCT GTG AAG GGG AGA GTG)SEQ ID NO:28, 5'-d(GTC TAT TAT TGT GCA AGA CAA GGC ACT ATA GCT GGT ATA CGT CAC TGG GGT CAA GGC AGC CTC)SEQ ID NO:29] were designed to replace each of the three complementarity determining regions (CDRs) in the NEW-based $V_H$ region that is part of the reshaped CAMPATH-1 antibody (Reichmann et al, 1988). A clone (FIG. 6) containing each of the three mutant oligonucleotides was identified by nucleotide sequencing. $CD4V_H NEW-Ser^{30}$ was created second by oligonucleotide-directed in vitro mutagenesis in the vector M13mp18 by priming with a single oligonucleotide on the 1458 base single-stranded cDNA template (FIG. 6) encoding $CD4V_H NEW-Thr^{30}$. Th oligonucleotide [5'-d(GCT TCA CCT TCA GCA ACT ATG GCA T)SEQ ID NO:30] was designed to mutate the residue at position 30 from threonine [ACC] to serine [AGC]. A clone (FIG. 7) containing this mutant oligonucleotide was identified by nucleotide sequencing. Double-stranded forms of the clones $CD4V_H NEW-Thr^{30}$ and $CD4V_H NEW-Ser^{30}$ were subcloned as HindIII fragments into the HindIII site of the expression vector pNH316. The vector pNH316 is a modified version of the vector pHβAPr-1 (Gunning et al, PNAS, 84: 4831–4835, 1987) which was engineered to contain a neomycin resistance gene driven by a metallothionine promoter.

Reshaped Heavy Chain Variable Regions Based on the Variable Region Framework of the Human Antibody KOL, and Expression Vector Constructs Two versions of the KOL-based reshaped heavy chain were created, $CD4V_H KOL-Thr^{113}$ and $CD4V_H KOL-Pro^{113}$. The $CD4V_H KOL-Thr^{113}$ version encodes a threonine residue at position 113 (FIG. 11) while the $CD4V_H KOL-Pro^{113}$ version encodes a proline residue at position 113 (FIG. 9). As a matter of convenience, $CD4V_H KOL-Thr^{113}$ was created first by oligonucleotide-directed in vitro mutagenesis of single-stranded DNA template containing the 817 base HindIII-BamHI fragment encoding the $V_H$ region of the rat CD4 antibody (FIG. 4) cloned into M13mp18 by priming simultaneously with five oligonucleotides [5'-d(CAC TCC CAG GTC CAA CTG GTG GAG TCT GGT GGA GGC GTG GTG GAG CCT GG)SEQ ID NO:31, 5'-d(AAG GTC CCT GAG ACT CTC CTG TTC CTC CTC TGG ATT CAT CTT CAG TAA CTA TGG CAT G)SEQ ID NO:32, 5'-d (GTC CGC CAG GCT CCA GGC AAG GGG CTG GAG TGG)SEQ ID NO:33, 5'-d(ACT ATC TCC AGA GAT AAT AGC AAA AAC ACC CTA TTC CTG CAA ATG G)SEQ ID NO:34, 5'-d(ACA GTC TGA GGC CCG AGG ACA CGG GCG TGT ATT TCT GTG CAA GAC AAG GGA C)SEQ ID NO:35] which were designed to replace the rat framework regions with the human framework regions of KOL. A clone containing each of the five mutant oligonucleotides was identified by nucleotide sequencing. $CD4V_H KOL-Pro^{113}$ was created second by oligonucleotide-directed in vitro mutagenesis of single-stranded DNA template containing the 817 base HindIII-BamHI fragment encoding $CD4V_H KOL-Thr^{113}$ cloned into M13mp18 by priming with the oligonucleotide [5'-d(TGG GGC CAA GGG ACC CCC GTC ACC GTC TCC TCA)SEQ ID NO:36]. A clone containing this mutant oligonucleotide was identified by nucleotide sequencing.

The immunoglobulin promoters were removed from the double-stranded DNA forms of clones encoding $CD4V_H KOL-Thr^{113}$ (FIG. 11) and $CD4V_H KOL-Pro^{113}$ (FIG. 9) by replacing (for both versions) the first 125 bp (HindIII-NcoI) with a HindIII-NcoI oligonucleotide linker fragment [5'-d(AGC TTT ACA GTT ACT GAG CAC ACA GGA CCT CAC)SEQ ID NO:37 and its overlapping complement 5'-d(CAT GGT GAG GTC CTG TGT GCT CAG TAA CTG TAA)SEQ ID NO:38]. The resultant clones, $CD4V_H KOL-Thr^{113}$ (FIG. 12) and $CD4V_H KOL-Pro^{113}$ (FIG. 10), now 731 bp HindIII-BamHI fragments, were separately subcloned into the HindIII and BamHI cloning sites of the expression vector pHβAPr-1-gpt (Gunning et al, PNAS USA 76, 1373, 1987) into which had been cloned the human IgG1 constant region gene (Bruggemann et al, J. Exp. Med. 166, 1351–1361, 1987) at the BamHI site. Thus, when transfected and expressed as antibody heavy chains (see below), these reshaped $V_H$ regions are linked to human IgG1 constant regions.

Fluorescence Activated Cell Sorter (FACS) Analysis

The relative affinities of the reshaped antibodies to bind the CD4 antigen were estimated by FACS analysis. The CD4-expressing cells used in this analysis were a cloned rat T cell line NB2-6TG stably transfected with an expression vector containing a complementary DNA (cDNA) encoding the human CD4 antigen (Maddon et al, Cell, 42, 93–104, 1985). Cells were stained with the appropriate reshaped antibody followed by fluorescein-conjugated sheep anti-human antibodies (Binding Site Ltd., Birmingham, UK). Control staining (see Table 1) consisted of no antibody present during the first stage of cell staining. Mean cellular fluorescence was determined with an Ortho FACS.

Antibody Avidity Analysis

The relative avidities of the rat YNB46.1.8 antibody and the reshaped $CD4V_H KOL-Thr^{113}$ antibody were estimated by an enzyme-linked immunosorbent assay (ELISA). Microtiter plates were coated with soluble recombinant CD4 antigen (Byrn et al, Nature, 344: 667–670, 1990) at 50 ul/well, 10 ug/ml, and then blocked with 100 ul/well phosphate buffered saline (PBS) containing 1.0% bovine serum albumin (BSA). Antibodies were diluted in PBS containing 0.1% BSA, and added to wells (50 ul/well) for 45 minutes at room temperature. Biotinylated CD4V$_H$KOL-Thr$^{113}$ antibody (10 ul/well; 20 ug/ml final concentration) was then added to each well for an additional 45 minutes. Wells were washed with PBS containing 0.1% BSA, and then 50 ul streptavidin-biotinylated horseradish peroxidase complex (Amersham; Aylesbury, UK) diluted 1:1,000 was added to each well for 30 minutes. Wells were washed with PBS containing 0.1% BSA, and 100 ul substrate (25 mM citric acid, 50 mM disodium hydrogen phosphate, 0.1% (w/v) o-phenylene diamine, 0.04% (v/v) 30% hydrogen peroxide) was added to each well. Reactions were stopped by the addition of 50 ul/well 1.0 M sulfuric acid. Optical densities at 492 nanometers (OD$_{492}$) were determined with an ELISA plate reader.

Transfections

Dihydrofolate reductase deficient chinese hamster ovary (CHO$^{DHFR-}$) cells (10$^6$/T-75 flask) were cotransfected as described (Wigler et al, PNAS USA 76, 1373, 1979) with 9 µg of heavy chain construct and 1 µg of the light chain construct. Transfectants were selected in medium containing 5% dialysed foetal bovine serum for 2 to 3 weeks, and antibody-secreting clones were identified by ELISAs of conditioned media. Antibody was concentrated and purified by protein-A Sepharose (Trade Mark) column chromatography.

2. Results

Cloning of Light and Heavy Chain Variable Region cDNAs cDNAs encoding the V$_L$ and V$_H$ regions from CD4 antibody-secreting hybridoma cells were isolated by PCR using primers which amplify the segment of mRNA encoding the N-terminal region through to the J region (Orlandi et al, 1989). V$_L$ and V$_H$ region PCR products were subcloned into the M13-based vectors M13V$_K$PCR3 and M13V$_H$PCR1, respectively. Initial nucleotide sequence analysis of random V$_L$ region clones revealed that most of the cDNAs encoded the V$_L$ region of the light chain expressed by the Y3-Ag 1.2.3 rat myeloma cell line (Crowe et al, Nucleic Acid Research, 17: 7992, 1989) that was used as the fusion partner to generate the anti-CD4 hybridoma. It is likely that the expression of the Y3-Ag 1.2.3 light chain mRNA is greater than that of the CD4 antibody light chain, or the Y3-Ag 1.2.3 light chain mRNA is preferentially amplified during the PCR.

To maximize the chance of finding CD4 V$_L$ region cDNAs, we first screened all M13 clones by hybridisation to a $^{32}$P-labeled oligonucleotide probe that is complementary to the CDR 2 of Y3-Ag 1.2.3 (Crowe et al, Nucleic Acid Research, 17: 7992, 1989). Subsequent sequence analysis was restricted to M13 clones which did not contain sequence complementary to this probe. In this manner, two cDNA clones from independent PCR amplifications were identified that encoded identical V$_L$ regions. Nucleotide sequence analysis of random V$_H$ region PCR products revealed a single species of V$_H$ region cDNA. Two V$_H$ cDNA clones from independent PCR amplifications were found to contain identical sequences except that the codon of residue 14 encoded proline [CCT] in one clone while the second clone encoded leucine [CTT] at the same position.

According to Kabat et al 1987, 524 of 595 sequenced V$_H$ regions contain a proline residue at this position, while only 6 contain leucine. We have therefore chosen the proline-encoding clone for illustration (see below). As residue 14 lies well within the first V$_H$ framework region and not in a CDR, it is unlikely to contribute directly to antigen binding, and the ambiguity at this position did not affect the subsequent reshaping strategy. Thus, we have not investigated this sequence ambiguity further.

The cDNA sequences and their predicted amino acid sequences are shown in FIGS. 1 and 4. As no additional V$_L$ or V$_H$ region-encoding clones were found, it was assumed that these sequences were derived from the CD4 antibody genes.

Construction of Reshaped Antibodies

Our goal was to investigate the importance of selecting the appropriate human V region framework during reshaping. Two reshaping strategies were employed.

First Reshaping Strategy

In the first strategy, we created a reshaped antibody that incorporated the CDRs from the rat-derived CD4 antibody and the same human V region framework sequences that we had previously successfully used for the reshaped CAMPATH-1 antibody, namely an REI-based framework for the V$_L$ region and an NEW-based framework for the V$_H$ region (Reichmann et al, 1988). This was accomplished by oligonucleotide-directed in vitro mutagenesis of the six CDRs of the reshaped CAMPATH-1 antibody light and heavy chain cDNAs shown in FIGS. 2 and 5, respectively. The resultant reshaped CD antibody light chain (FIG. 3) is called CD4V$_L$REI. Two versions of the NEW-based reshaped CD4 antibody heavy chain were created: CD4V$_H$NEW-Thr$^{30}$ (FIG. 6) encoding a threonine residue at position 30 (in framework 1) and CD4V$_H$NEW-Ser$^{30}$ (FIG. 7) encoding a serine residue at position 30. These two different versions were created because the successfully reshaped CAMPATH-1 antibody heavy chain bound antigen well whether position 30 encoded a threonine or serine residue (Reichmann et al, 1988), and we chose to test both possibilities in this case as well.

Second Reshaping Strategy

In the second reshaping strategy, we have reshaped the CD4 antibody V$_H$ region to contain the V$_H$ region framework sequences of the human antibody KOL. Of all known human antibody V$_H$ regions, the overall amino acid sequence of the V$_H$ region of KOL is most homologous to the rat CD4 antibody V$_H$ region. The V$_H$ regions of the human antibodies KOL and NEW are 66% and 42% homologous to the rat CD4 antibody V$_H$ region, respectively.

Two versions of the KOL-based reshaped CD4 antibody heavy chain V region were created that differ by a single amino acid residue within the fourth framework region: CD4V$_H$KOL-Pro$^{113}$ (FIG. 10) encodes a proline residue at position 113 and CD4V$_H$KOL-Thr$^{113}$ (FIG. 12) encodes a threonine residue at position 113. CD4V$_H$KOL-Pro$^{113}$ is "true to form" in that its framework sequences are identical to those of the KOL antibody heavy chain V region (FIG. 8).

Of all known human antibody V$_L$ regions, the overall amino acid sequence of the V$_L$ region of the human light chain NEW is most homologous (67%) to the rat CD4 antibody $V_L$ region. Thus, the identical reshaped light chain, $CD4V_L REI$ (described above), that was expressed with the NEW-based reshaped CD4 antibody heavy chains $CD4V_H NEW-Thr^{30}$ and $CD4V_H NEW-Ser^{30}$, is also expressed with the KOL-based reshaped CD4 antibody heavy chains $CD4V_H KOL-Pro^{113}$ and $CD4V_H KOL-Thr^{113}$. This is advantageous because expression of the same reshaped light chain with different reshaped heavy chains allows for a direct functional comparison of each reshaped heavy chain.

To summarise, four different reshaped antibodies were created. The reshaped light chain of each antibody is called $CD4V_L REI$. The reshaped heavy chains of the antibodies are called $CD4V_H NEW-Thr^{30}$, $CD4V_H NEW-Ser^{30}$, $CD4V_H KOL-Pro^{113}$, and $CD4V_H KOL-Thr^{113}$, respectively. Each of the reshaped heavy chains contain the same human IgG1 constant region. As each reshaped antibody contains the same reshaped light chain, the name of a reshaped antibody's heavy chain shall be used below to refer to the whole antibody (heavy and light chain combination).

Relative Affinities of the Reshaped Antibodies

The relative affinities of the reshaped antibodies were approximated by measuring their ability to bind to CD4 antigen-expressing cells at various antibody concentrations. FACS analysis determined the mean cellular fluorescence of the stained cells (Table 1).

It is clear from this analysis that the reshaped CD4 antibodies bind to CD4 antigen to varying degrees over a broad concentration range. Consider Experiment 1 of Table 1 first. Comparing $CD4V_H KOL-Thr^{113}$ antibody to $CD4V_H NEW-Thr^{30}$ antibody, it is clear that both antibodies bind CD4+ cells when compared to the control, reshaped CAMPATH-1 antibody. However, $CD4V_H KOL-Thr^{113}$ antibody binds CD4+ cells with far greater affinity than $CD4V_H NEW-Thr^{30}$ antibody. The lowest concentration of $CD4V_H KOL-Thr^{113}$ antibody tested (2.5 ug/ml) gave a mean cellular fluorescence nearly equivalent to that of the highest concentration of $CD4V_H NEW-Thr^{30}$ antibody tested (168 ug/ml). Experiment 2 demonstrates that $CD4V_H NEW-Ser^{30}$ antibody may bind CD4+ cells somewhat better than $CD4V_H NEW-Thr^{30}$. Only 2.5 ug/ml $CD4V_H NEW-Ser^{30}$ antibody is required to give a mean cellular fluorescence nearly equivalent to 10 ug/ml $CD4V_H NEW-Thr^{30}$ antibody. Experiment 3 demonstrates that $CD4V_H KOL-Thr^{113}$ antibody may bind CD4+ cells somewhat better than $CD4V_H KOL-Pro^{113}$ antibody.

From these assays, it is clear that the KOL-based reshaped antibodies are far superior to the NEW-based reshaped antibodies with regards to affinity towards CD4+ cells. Also, there is a lesser difference, if any, between $CD4V_H NEW-Thr^{30}$ antibody and $CD4V_H NEW-Ser^{30}$ antibody, and likewise between $CD4V_H KOL-Thr^{113}$ antibody and $CD4V_H KOL-Pro^{113}$ antibody. A ranking of these reshaped antibodies can thus be derived based on their relative affinities for CD4+ cells:

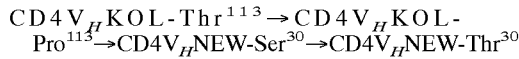

It should be restated that each of the reshaped CD4 antibodies used in the above experiments have the identical heavy chain constant regions, and are associated with identical reshaped light chains. Thus observed differences of binding to CD4+ cells must be due to differences in their heavy chain V regions.

Relative Avidities of the Rat YNB46.1.8 Antibody and the Reshaped $CD4V_H KOL-Thr^{113}$ Antibody The relative avidities of the rat YNB46.1.8 antibody and the reshaped $CD4V_H KOL-Thr^{113}$ antibody were estimated by ELISA. In this assay, the ability of each antibody to inhibit the binding of biotinylated $CD4V_H KOL-Thr^{113}$ antibody to soluble recombinant CD4 antigen was determined. Results of an experiment are shown in FIG. 13. The inhibition of binding of biotinylated $CD4V_H KOL-Thr^{113}$ antibody was linear for both the unlabeled $CD4V_H KOL-Thr^{113}$ and YNB46.1.8 antibodies near the optical density of 0.3. The concentrations of $CD4V_H KOL-Thr^{113}$ and YNB46.1.8 antibodies that give an optical density of 0.3 are 28.7 and 1.56 ug/ml, respectively. Thus the avidity of the YNB46.1.8 antibody can be estimated to be 28.7/1.56 or about 18 times better than that of $CD4V_H KOL-Thr^{113}$ antibody. It should be noted that this experiment only provides a rough approximation of relative avidities, not affinities. The rat YNB46.1.8 antibody contains a different constant region than that of the $CD4V_H KOL-Thr^{113}$ antibody, and this could affect how well the antibodies bind CD4 antigen, irrespective of their actual affinities for CD4 antigen. The actual affinity of the reshaped antibodies for CD4 antigen may be greater, lesser, or the same as the YNB46.1.8 antibody. The other reshaped antibodies $CD4V_H KOL-Pro^{113}$, $CD4V_H NEW-Ser^{30}$, and $CD4V_H NEW-Thr^{30}$ have not yet been tested in this assay.

TABLE 1

Mean cellular fluorescence of CD4+ cells stained with reshaped antibodies

| Reshaped Antibody | Concentration (μg/ml) | Mean cellular Fluorescence |
|---|---|---|
| Experiment 1. | | |
| $CD4V_H KOL-Thr^{113}$ | 113 | 578.0 |
| $CD4V_H KOL-Thr^{113}$ | 40 | 549.0 |
| $CD4V_H KOL-Thr^{113}$ | 10 | 301.9 |
| $CD4V_H KOL-Thr^{113}$ | 2.5 | 100.5 |
| $CD4V_H NEW-Thr^{30}$ | 168 | 97.0 |
| $CD4V_H NEW-Thr^{30}$ | 40 | 40.4 |
| $CD4V_H NEW-Thr^{30}$ | 10 | 18.7 |
| $CD4V_H NEW-Thr^{30}$ | 2.5 | 10.9 |
| CAMPATH-1 | 100 | 11.6 |
| CAMPATH-1 | 40 | 9.4 |
| CAMPATH-1 | 10 | 9.0 |
| CAMPATH-1 | 2.5 | 8.6 |
| CONTROL | — | 9.0 |
| Experiment 2. | | |
| $CD4V_H NEW-Thr^{30}$ | 168 | 151.3 |
| $CD4V_H NEW-Thr^{30}$ | 40 | 81.5 |
| $CD4V_H NEW-Thr^{30}$ | 10 | 51.0 |
| $CD4V_H NEW-Thr^{30}$ | 2.5 | 39.3 |
| $CD4V_H NEW-Ser^{30}$ | 160 | 260.2 |
| $CD4V_H NEW-Ser^{30}$ | 40 | 123.5 |
| $CD4V_H NEW-Ser^{30}$ | 10 | 68.6 |
| $CD4V_H NEW-Ser^{30}$ | 2.5 | 49.2 |
| CONTROL | — | 35.8 |
| Experiment 3. | | |
| $CD4V_H KOL-Pro^{113}$ | 100 | 594.9 |
| $CD4V_H KOL-Pro^{113}$ | 40 | 372.0 |
| $CD4V_H KOL-Pro^{113}$ | 10 | 137.7 |
| $CD4V_H KOL-Pro^{113}$ | 2.5 | 48.9 |
| $CD4V_H KOL-Thr^{113}$ | 100 | 696.7 |
| $CD4V_H KOL-Thr^{113}$ | 40 | 631.5 |
| $CD4V_H KOL-Thr^{113}$ | 10 | 304.1 |
| $CD4V_H KOL-Thr^{113}$ | 2.5 | 104.0 |
| CONTROL | — | 12.3 |

What is claimed is:

1. An antibody which is capable of binding to human CD4 antigen, in which the CDRs of the light chain of the antibody have the amino acid sequences:
   CDR1: LASEDIYSDLA (SEQ ID NO:13)
   CDR2: NTDTLQN (SEQ ID NO:14)
   CDR3: QQYNNYPWT (SEQ ID NO:15)
in which the CDRs of the heavy chain of the antibody have the amino acid sequences:
   CDR1: NYGMA (SEQ ID NO:16)
   CDR2: TISHDGSDTYFRDSVKG (SEQ ID NO:17)
   CDR3: QGTIAGIRH (SEQ ID NO:18), and
in which the framework of the variable domain of each chain and any constant domain present in said chain are derived from a mammalian non-rat species.

2. An antibody according to claim 1, in which the mammalian non-rat species is human.

3. An antibody according to claim 2, in which the variable domain framework region of the heavy chain consists essentially of the heavy chain variable domain framework region of the protein KOL.

4. An antibody according to claim 3, in which the heavy chain variable domain has the amino acid sequence shown in the upper line in FIG. 10 (SEQ ID NO:39) or 12 (SEQ ID NO:40).

5. An antibody according to claim 2, in which the variable domain framework region of the heavy chain consists essentially of the heavy chain variable domain framework region of the protein NEW.

6. An antibody according to claim 5, in which the heavy chain variable domain has the amino acid sequence shown in the upper line of FIG. 6 (SEQ ID NO:41) or 7 (SEQ ID NO:42).

7. An antibody according to claims 2, 3, 4, 5 or 6, in which the variable domain framework of the light chain consists essentially of the variable domain framework of the protein REI.

8. An antibody according to claim 7, in which the light chain has the amino acid sequence shown in the upper line of FIG. 3 (SEQ ID NO:43).

9. A pharmaceutical composition comprising a pharmaceutically acceptable carrier or diluent and, as active ingredient, an antibody as claimed in claim 1.

10. An antibody which is capable of binding to human CD4 antigen, in which the CDRs of the light chain of the antibody have the amino acid sequences:
    CDR1: LASEDIYSDLA (SEQ ID NO:13)
    CDR2: NTDTLQN (SEQ ID NO:14)
    CDR3: QQYNNYPWT (SEQ ID NO:15), and
in which the CDRs of the heavy chain of the antibody have the amino acid sequences:
    CDR1: NYGMA (SEQ ID NO:16)
    CDR2: TISHDGSDTYFRDSVKG (SEQ ID NO:17)
    CDR3: QCTIAGIRH (SEQ ID NO:18), and
in which the framework of the variable domain of each chain and the constant region of said chain are derived from a human.

11. An antibody according to claim 1, wherein the antibody has glycosylation characteristic of CHO cells.

* * * * *

SEQUENCE LISTING (1) GENERAL INFORMATION:

(iii) NUMBER OF SEQUENCES: 43

(2) INFORMATION FOR SEQ ID NO:1:

(i) SEQUENCE CHARACTERISTICS:
       (A) LENGTH: 620 base pairs
       (B) TYPE: nucleic acid
       (C) STRANDEDNESS: both
       (D) TOPOLOGY: linear (ii) MOLECULE TYPE: cDNA (vi) ORIGINAL SOURCE:
       (G) CELL TYPE: Hybridoma
       (H) CELL LINE: YNB46.1.8

(xi) SEQUENCE DESCRIPTION: SEQ ID NO:1:

```
AAGCTTATGA ATATGCAAAT CCTCTGAATC TACATGGTAA ATATAGGTTT GTCTATACCA      60
CAAACAGAAA AACATGAGAT CACAGTTCTC TCTACAGTTA CTGAGCACAC AGGACCTCAC     120
CATGGGATGG AGCTGTATCA TCCTCTTCTT GGTAGCAACA GCTACAGGTA AGGGGTGCAC     180
AGTAGCAGGC TTGAGGTCTG GACATATATA TGGGTGACAA TGCATCCAC TTTGCCTTTC      240
TCTCCACAGG TGTCCACTCC GACATCCAGC TGACCCAGTC TCCAGTTTCC CTGTCTGCAT     300
CTCTGGGAGA AACTGTCAAC ATCGAATGTC TAGCAAGTGA GGACATTTAC AGTGATTTAG     360
CATGGTATCA GCAGAAGCCA GGGAAATCTC CTCAACTCCT GATCTATAAT ACAGATACCT     420
TGCAAAATGG GGTCCCTTCA CGGTTTAGTG GCAGTGGATC TGGCACACAG TATTCTCTAA     480
AAATAAACAG CCTGCAATCT GAAGATGTCG CGACTTATTT CTGTCAACAA TATAACAATT     540
ATCCGTGGAC GTTCGGTGGA GGGACCAAGC TGGAGATCAA ACGTGAGTAG AATTTAAACT     600
TTGCTTCCTC AGTTGGATCC                                                 620
```

(2) INFORMATION FOR SEQ ID NO:2:

(i) SEQUENCE CHARACTERISTICS:
       (A) LENGTH: 748 base pairs
       (B) TYPE: nucleic acid
       (C) STRANDEDNESS: both
       (D) TOPOLOGY: linear (ii) MOLECULE TYPE: cDNA (xi) SEQUENCE DESCRIPTION: SEQ ID NO:2:

```
AAGCTTGGCT CTACAGTTAC TGAGCACACA GGACCTCACC ATGGGATGGA GCTGTATCAT      60
CCTCTTCTTG GTAGCAACAG CTACAGGTGT CCACTCCGAC ATCCAGATGA CCCAGAGCCC     120
AAGCAGCCTG AGCGCCAGCG TGGGTGACAG AGTGACCATC ACCTGTAAAG CAAGTCAGAA     180
TATTGACAAA TACTTAAACT GGTACCAGCA GAAGCCAGGT AAGGCTCCAA AGCTGCTGAT     240
CTACAATACA AACAATTTGC AAACGGGTGT GCCAAGCAGA TTCAGCGGTA GCGGTAGCGG     300
TACCGACTTC ACCTTCACCA TCAGCAGCCT CCAGCCAGAG GACATCGCCA CCTACTACTG     360
CTTGCAGCAT ATAAGTAGGC CGCGCACGTT CGGCCAAGGG ACCAAGGTGG AAATCAAACG     420
AACTGTGGCT GCACCATCTG TCTTCATCTT CCCGCCATCT GATGAGCAGT TGAAATCTGG     480
AACTGCCTCT GTTGTGTGCC TGCTGAATAA CTTCTATCCC AGAGAGGCCA AGTACAGTG      540
GAAGGTGGAT AACGCCCTCC AATCGGGTAA CTCCCAGGAG AGTGTCACAG AGCAGGACAG     600
```

-continued

```
CAAGGACAGC ACCTACAGCC TCAGCAGCAC CCTGACGCTG AGCAAAGCAG ACTACGAGAA      660

ACACAAAGTC TACGCCTGCG AAGTCACCCA TCAGGGCCTG AGCTCGCCCG TCACAAAGAG      720

CTTCAACAGG GGAGAGTGTT AGAAGCTT                                        748
```

(2) INFORMATION FOR SEQ ID NO:3:

(i) SEQUENCE CHARACTERISTICS:
        (A) LENGTH: 748 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 41..742

(xi) SEQUENCE DESCRIPTION: SEQ ID NO:3:

```
AAGCTTGGCT CTACAGTTAC TGAGCACACA GGACCTCACC ATG GGA TGG AGC TGT       55
                                            Met Gly Trp Ser Cys
                                              1               5

ATC ATC CTC TTC TTG GTA GCA ACA GCT ACA GGT GTC CAC TCC GAC ATC      103
Ile Ile Leu Phe Leu Val Ala Thr Ala Thr Gly Val His Ser Asp Ile
             10                  15                  20

CAG ATG ACC CAG AGC CCA AGC AGC CTG AGC GCC AGC GTG GGT GAC AGA      151
Gln Met Thr Gln Ser Pro Ser Ser Leu Ser Ala Ser Val Gly Asp Arg
         25                  30                  35

GTG ACC ATC ACC TGT CTA GCA AGT GAG GAC ATT TAC AGT GAT TTA GCA      199
Val Thr Ile Thr Cys Leu Ala Ser Glu Asp Ile Tyr Ser Asp Leu Ala
     40                  45                  50

TGG TAC CAG CAG AAG CCA GGT AAG GCT CCA AAG CTG CTG ATC TAC AAT      247
Trp Tyr Gln Gln Lys Pro Gly Lys Ala Pro Lys Leu Leu Ile Tyr Asn
 55                  60                  65

ACA GAT ACC TTG CAA AAT GGT GTG CCA AGC AGA TTC AGC GGT AGC GGT      295
Thr Asp Thr Leu Gln Asn Gly Val Pro Ser Arg Phe Ser Gly Ser Gly
 70                  75                  80                  85

AGC GGT ACC GAC TTC ACC TTC ACC ATC AGC AGC CTC CAG CCA GAG GAC      343
Ser Gly Thr Asp Phe Thr Phe Thr Ile Ser Ser Leu Gln Pro Glu Asp
                 90                  95                 100

ATC GCC ACC TAC TAC TGC CAA CAG TAT AAC AAT TAT CCG TGG ACG TTC      391
Ile Ala Thr Tyr Tyr Cys Gln Gln Tyr Asn Asn Tyr Pro Trp Thr Phe
            105                 110                 115

GGC CAA GGG ACC AAG GTG GAA ATC AAA CGA ACT GTG GCT GCA CCA TCT      439
Gly Gln Gly Thr Lys Val Glu Ile Lys Arg Thr Val Ala Ala Pro Ser
        120                 125                 130

GTC TTC ATC TTC CCG CCA TCT GAT GAG CAG TTG AAA TCT GGA ACT GCC     487
Val Phe Ile Phe Pro Pro Ser Asp Glu Gln Leu Lys Ser Gly Thr Ala
    135                 140                 145

TCT GTT GTG TGC CTG CTG AAT AAC TTC TAT CCC AGA GAG GCC AAA GTA      535
Ser Val Val Cys Leu Leu Asn Asn Phe Tyr Pro Arg Glu Ala Lys Val
150                 155                 160                 165

CAG TGG AAG GTG GAT AAC GCC CTC CAA TCG GGT AAC TCC CAG GAG AGT      583
Gln Trp Lys Val Asp Asn Ala Leu Gln Ser Gly Asn Ser Gln Glu Ser
                170                 175                 180

GTC ACA GAG CAG GAC AGC AAG GAC AGC ACC TAC AGC CTC AGC AGC ACC      631
Val Thr Glu Gln Asp Ser Lys Asp Ser Thr Tyr Ser Leu Ser Ser Thr
            185                 190                 195
```

| | | | | | | | | | | |
|---|---|---|---|---|---|---|---|---|---|---|
|CTG|ACG|CTG|AGC|AAA|GCA|GAC|TAC|GAG|AAA|CAC|AAA|GTC|TAC|GCC|TGC|679|
|Leu|Thr|Leu|Ser|Lys|Ala|Asp|Tyr|Glu|Lys|His|Lys|Val|Tyr|Ala|Cys| |
| | | |200| | | |205| | | | |210| | | | |

```
GAA GTC ACC CAT CAG GGC CTG AGC TCG CCC GTC ACA AAG AGC TTC AAC     727
Glu Val Thr His Gln Gly Leu Ser Ser Pro Val Thr Lys Ser Phe Asn
    215                 220                 225

AGG GGA GAG TGT TAGAAGCTT                                           748
Arg Gly Glu Cys
230
```

(2) INFORMATION FOR SEQ ID NO:4:

(i) SEQUENCE CHARACTERISTICS:
        (A) LENGTH: 817 base pairs
        (B) TYPE: nucleic acid
        (C) STRANDEDNESS: both
        (D) TOPOLOGY: linear (ii) MOLECULE TYPE: DNA (genomic)

(xi) SEQUENCE DESCRIPTION: SEQ ID NO:4:

```
AAGCTTATGA ATATGCAAAT CCTCTGAATC TACATGGTAA ATATAGGTTT GTCTATACCA      60

CAAACAGAAA AACATGAGAT CACAGTTCTC TCTACAGTTA CTCAGCACAC AGGACCTCAC     120

CATGGGATGG AGCTGTATCA TCCTCTTCTT GGTAGCAACA GCTACAGGTA AGGGGCTCAC     180

AGTAGCAGGC TTGAGGTCTG ACATATATA TGGGTGACAA TGACATCCAC TTTGCCTTTC      240

TCTCCACAGG TGTCCACTCC CAGGTCCAAC TGCAGGAGTC TGGTGGAGGC TTAGTGCAGC     300

CTGGAAGGTC CCTGAAACTC TCCTGTGCAG CCTCTGGACT CACTTTCAGT AACTATGGCA     360

TGGCCTGGGT CCGCCAGGCT CCAACGAAGG GGCTGGAGTG GGTCGCAACC ATTAGTCATG     420

ATGGTAGTGA CACTTACTTT CGAGACTCCG TGAAGGGCCG ATTCACTATC TCCAGAGATA     480

ATGGAAAAAG CACCCTATAC CTGCAAATGG ACAGTCTGAG GTCTGAGGAC ACGGCCACTT     540

ATTACTGTGC AAGACAAGGG ACTATAGCAG GTATACGTCA CTGGGGCCAA GGGACCACGG     600

TCACCGTCTC CTCAGGTGAG TCCTTACAAC CTCTCTCTTC TATTCAGCTT AAATAGATTT     660

TACTGCATTT GTTGGGGGGG AAATGTGTGT ATCTGAATTT CAGGTCATGA AGGACTAGGG     720

ACACCTTGGG AGTCAGAAAG GGTCATTGGG AGCCCGGGCT GATGCAGACA GACATCCTCA     780

GCTCCCAGAC TTCATGGCCA GAGATTTATA GGGATCC                              817
```

(2) INFORMATION FOR SEQ ID NO:5:

(i) SEQUENCE CHARACTERISTICS:
        (A) LENGTH: 1467 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:5:

```
AAGCTTTACA GTTACTGAGC ACACAGGACC TCACCATGGG ATGGAGCTGT ATCATCCTCT      60

TCTTGGTAGC AACAGCTACA GGTGTCCACT CCCAGGTCCA ACTGCAGGAG AGCGGTCCAG     120

GTCTTGTGAG ACCTAGCCAG ACCCTGAGCC TGACCTGCAC CGTGTCTGGC TTCACCTTCA     180

CCGATTTCTA CATGAACTGG GTGAGACAGC CACCTGGACG AGGTCTTGAG TGGATTGGAT     240

TTATTAGAGA CAAAGCTAAA GGTTACACAA CAGAGTACAA TCCATCTGTG AAGGGGAGAG     300

TGACAATGCT GGTAGACACC AGCAAGAACC AGTTCAGCCT GAGACTCAGC AGCGTGACAG     360

CCGCCGACAC CGCGGTCTAT TATTGTGCAA GAGAGGGCCA CACTGCTGCT CCTTTTGATT     420
```

-continued

```
ACTGGGGTCA AGGCAGCCTC GTCACAGTCT CCTCAGCCTC CACCAAGGGC CCATCGGTCT    480

TCCCCCTGGC ACCCTCCTCC AAGAGCACCT CTGGGGGCAC AGCGGCCCTG GGCTGCCTGG    540

TCAAGGACTA CTTCCCCGAA CCGGTGACGG TGTCGTGGAA CTCAGGCGCC CTGACCAGCG    600

GCGTGCACAC CTTCCCGGCT GTCCTACAGT CCTCAGGACT CTACTCCCTC AGCAGCGTGG    660

TGACCGTGCC CTCCAGCAGC TTGGGCACCC AGACCTACAT CTGCAACGTG AATCACAAGC    720

CCAGCAACAC CAAGGTGGAC AAGAAAGTTG AGCCCAAATC TTGTGACAAA ACTCACACAT    780

GCCCACCGTG CCCAGCACCT GAACTCCTGG GGGGACCGTC AGTCTTCCTC TTCCCCCCAA    840

AACCCAAGGA CACCCTCATG ATCTCCCGGA CCCCTGAGGT CACATGCGTG GTGGTGGACG    900

TGAGCCACGA AGACCCTGAG GTCAAGTTCA ACTGGTACGT GGACGGCGTG GAGGTGCATA    960

ATGCCAAGAC AAAGCCGCGG GAGGAGCAGT ACAACAGCAC GTACCGTGTG GTCAGCGTCC   1020

TCACCGTCCT GCACCAGGAC TGGCTGAATG GCAAGGAGTA CAAGTGCAAG GTCTCCAACA   1080

AAGCCCTCCC AGCCCCCATC GAGAAAACCA TCTCCAAAGC CAAAGGGCAG CCCCGAGAAC   1140

CACAGGTGTA CACCCTGCCC CCATCCCGGG ATGAGCTGAC CAAGAACCAG GTCAGCCTGA   1200

CCTGCCTGGT CAAAGGCTTC TATCCCAGCG ACATCGCCGT GGAGTGGGAG AGCAATGGGC   1260

AGCCGGAGAA CAACTACAAG ACCACGCCTC CCGTGCTGGA CTCCGACGGC TCCTTCTTCC   1320

TCTACAGCAA GCTCACCGTG GACAAGAGCA GGTGGCAGCA GGGGAACGTC TTCTCATGCT   1380

CCGTGATGCA TGAGGCTCTG CACAACCACT ACACGCAGAA GAGCCTCTCC CTGTCTCCGG   1440

GTAAATGAGT GCGACGGCCC CAAGCTT                                      1467
```

(2) INFORMATION FOR SEQ ID NO:6:

(i) SEQUENCE CHARACTERISTICS:
        (A) LENGTH: 1458 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 36..1439

(xi) SEQUENCE DESCRIPTION: SEQ ID NO:6:

```
AAGCTTTACA GTTACTGAGC ACACAGGACC TCACC ATG GGA TGG AGC TGT ATC         53
                                       Met Gly Trp Ser Cys Ile
                                         1               5

ATC CTC TTC TTG GTA GCA ACA GCT ACA GGT GTC CAC TCC CAG GTC CAA       101
Ile Leu Phe Leu Val Ala Thr Ala Thr Gly Val His Ser Gln Val Gln
            10                  15                  20

CTG CAG GAG AGC GGT CCA GGT CTT GTG AGA CCT AGC CAG ACC CTG AGC       149
Leu Gln Glu Ser Gly Pro Gly Leu Val Arg Pro Ser Gln Thr Leu Ser
        25                  30                  35

CTG ACC TGC ACC GTG TCT GGC TTC ACC TTC ACC AAC TAT GGC ATG GCC       197
Leu Thr Cys Thr Val Ser Gly Phe Thr Phe Thr Asn Tyr Gly Met Ala
    40                  45                  50

TGG GTG AGA CAG CCA CCT GGA CGA GGT CTT GAG TGG ATT GGA ACC ATT       245
Trp Val Arg Gln Pro Pro Gly Arg Gly Leu Glu Trp Ile Gly Thr Ile
55                  60                  65                  70

AGT CAT GAT GGT AGT GAC ACT TAC TTT CGA GAC TCT GTG AAG GGG AGA       293
```

-continued

```
                Ser His Asp Gly Ser Asp Thr Tyr Phe Arg Asp Ser Val Lys Gly Arg
                             75                  80                  85

GTG ACA ATG CTG GTA GAC ACC AGC AAG AAC CAG TTC AGC CTG AGA CTC                341
Val Thr Met Leu Val Asp Thr Ser Lys Asn Gln Phe Ser Leu Arg Leu
             90                  95                 100

AGC AGC GTG ACA GCC GCC GAC ACC GCG GTC TAT TAT TGT GCA AGA CAA                389
Ser Ser Val Thr Ala Ala Asp Thr Ala Val Tyr Tyr Cys Ala Arg Gln
            105                 110                 115

GGC ACT ATA GCT GGT ATA CGT CAC TGG GGT CAA GGC AGC CTC GTC ACA                437
Gly Thr Ile Ala Gly Ile Arg His Trp Gly Gln Gly Ser Leu Val Thr
        120                 125                 130

GTC TCC TCA GCC TCC ACC AAG GGC CCA TCG GTC TTC CCC CTG GCA CCC                485
Val Ser Ser Ala Ser Thr Lys Gly Pro Ser Val Phe Pro Leu Ala Pro
135                 140                 145                 150

TCC TCC AAG AGC ACC TCT GGG GGC ACA GCG GCC CTG GGC TGC CTG GTC                533
Ser Ser Lys Ser Thr Ser Gly Gly Thr Ala Ala Leu Gly Cys Leu Val
                155                 160                 165

AAG GAC TAC TTC CCC GAA CCG GTG ACG GTG TCG TGG AAC TCA GGC GCC                581
Lys Asp Tyr Phe Pro Glu Pro Val Thr Val Ser Trp Asn Ser Gly Ala
            170                 175                 180

CTG ACC AGC GGC GTG CAC ACC TTC CCG GCT GTC CTA CAG TCC TCA GGA                629
Leu Thr Ser Gly Val His Thr Phe Pro Ala Val Leu Gln Ser Ser Gly
        185                 190                 195

CTC TAC TCC CTC AGC AGC GTG GTG ACC GTG CCC TCC AGC AGC TTG GGC                677
Leu Tyr Ser Leu Ser Ser Val Val Thr Val Pro Ser Ser Ser Leu Gly
    200                 205                 210

ACC CAG ACC TAC ATC TGC AAC GTG AAT CAC AAG CCC AGC AAC ACC AAG                725
Thr Gln Thr Tyr Ile Cys Asn Val Asn His Lys Pro Ser Asn Thr Lys
215                 220                 225                 230

GTG GAC AAG AAA GTT GAG CCC AAA TCT TGT GAC AAA ACT CAC ACA TGC                773
Val Asp Lys Lys Val Glu Pro Lys Ser Cys Asp Lys Thr His Thr Cys
                235                 240                 245

CCA CCG TGC CCA GCA CCT GAA CTC CTG GGG GGA CCG TCA GTC TTC CTC                821
Pro Pro Cys Pro Ala Pro Glu Leu Leu Gly Gly Pro Ser Val Phe Leu
            250                 255                 260

TTC CCC CCA AAA CCC AAG GAC ACC CTC ATG ATC TCC CGG ACC CCT GAG                869
Phe Pro Pro Lys Pro Lys Asp Thr Leu Met Ile Ser Arg Thr Pro Glu
        265                 270                 275

GTC ACA TGC GTG GTG GTG GAC GTG AGC CAC GAA GAC CCT GAG GTC AAG                917
Val Thr Cys Val Val Val Asp Val Ser His Glu Asp Pro Glu Val Lys
    280                 285                 290

TTC AAC TGG TAC GTG GAC GGC GTG GAG GTG CAT AAT GCC AAG ACA AAG                965
Phe Asn Trp Tyr Val Asp Gly Val Glu Val His Asn Ala Lys Thr Lys
295                 300                 305                 310

CCG CGG GAG GAG CAG TAC AAC AGC ACG TAC CGT GTG GTC AGC GTC CTC                1013
Pro Arg Glu Glu Gln Tyr Asn Ser Thr Tyr Arg Val Val Ser Val Leu
                315                 320                 325

ACC GTC CTG CAC CAG GAC TGG CTG AAT GGC AAG GAG TAC AAG TGC AAG                1061
Thr Val Leu His Gln Asp Trp Leu Asn Gly Lys Glu Tyr Lys Cys Lys
            330                 335                 340

GTC TCC AAC AAA GCC CTC CCA GCC CCC ATC GAG AAA ACC ATC TCC AAA                1109
Val Ser Asn Lys Ala Leu Pro Ala Pro Ile Glu Lys Thr Ile Ser Lys
        345                 350                 355

GCC AAA GGG CAG CCC CGA GAA CCA CAG GTG TAC ACC CTG CCC CCA TCC                1157
Ala Lys Gly Gln Pro Arg Glu Pro Gln Val Tyr Thr Leu Pro Pro Ser
    360                 365                 370

CGG GAT GAG CTG ACC AAG AAC CAG GTC AGC CTG ACC TGC CTG GTC AAA                1205
Arg Asp Glu Leu Thr Lys Asn Gln Val Ser Leu Thr Cys Leu Val Lys
375                 380                 385                 390
```

-continued

```
GGC TTC TAT CCC AGC GAC ATC GCC GTG GAG TGG GAG AGC AAT GGG CAG        1253
Gly Phe Tyr Pro Ser Asp Ile Ala Val Glu Trp Glu Ser Asn Gly Gln
            395                 400                 405

CCG GAG AAC AAC TAC AAG ACC ACG CCT CCC GTG CTG GAC TCC GAC GGC        1301
Pro Glu Asn Asn Tyr Lys Thr Thr Pro Pro Val Leu Asp Ser Asp Gly
        410                 415                 420

TCC TTC TTC CTC TAC AGC AAG CTC ACC GTG GAC AAG AGC AGG TGG CAG        1349
Ser Phe Phe Leu Tyr Ser Lys Leu Thr Val Asp Lys Ser Arg Trp Gln
    425                 430                 435

CAG GGG AAC GTC TTC TCA TGC TCC GTG ATG CAT GAG GCT CTG CAC AAC        1397
Gln Gly Asn Val Phe Ser Cys Ser Val Met His Glu Ala Leu His Asn
440                 445                 450

CAC TAC ACG CAG AAG AGC CTC TCC CTG TCT CCG GGT AAA TGAGTGCGAC         1446
His Tyr Thr Gln Lys Ser Leu Ser Leu Ser Pro Gly Lys
455                 460                 465

GGCCCCAAGC TT                                                          1458
```

(2) INFORMATION FOR SEQ ID NO:7:

(i) SEQUENCE CHARACTERISTICS:
        (A) LENGTH: 1458 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (ix) FEATURE:
        (A) NAME/KEY: CDS
        (B) LOCATION: 36..1439

(xi) SEQUENCE DESCRIPTION: SEQ ID NO:7:

```
AAGCTTTACA GTTACTGAGC ACACAGGACC TCACC ATG GGA TGG AGC TGT ATC          53
                                      Met Gly Trp Ser Cys Ile
                                        1               5

ATC CTC TTC TTG GTA GCA ACA GCT ACA GGT GTC CAC TCC CAG GTC CAA        101
Ile Leu Phe Leu Val Ala Thr Ala Thr Gly Val His Ser Gln Val Gln
            10                  15                  20

CTG CAG GAG AGC GGT CCA GGT CTT GTG AGA CCT AGC CAG ACC CTG AGC        149
Leu Gln Glu Ser Gly Pro Gly Leu Val Arg Pro Ser Gln Thr Leu Ser
        25                  30                  35

CTG ACC TGC ACC GTG TCT GGC TTC ACC TTC AGC AAC TAT GGC ATG GCC        197
Leu Thr Cys Thr Val Ser Gly Phe Thr Phe Ser Asn Tyr Gly Met Ala
    40                  45                  50

TGG GTG AGA CAG CCA CCT GGA CGA GGT CTT GAG TGG ATT GGA ACC ATT        245
Trp Val Arg Gln Pro Pro Gly Arg Gly Leu Glu Trp Ile Gly Thr Ile
55                  60                  65                  70

AGT CAT GAT GGT AGT GAC ACT TAC TTT CGA GAC TCT GTG AAG GGG AGA        293
Ser His Asp Gly Ser Asp Thr Tyr Phe Arg Asp Ser Val Lys Gly Arg
            75                  80                  85

GTG ACA ATG CTG GTA GAC ACC AGC AAG AAC CAG TTC AGC CTG AGA CTC        341
Val Thr Met Leu Val Asp Thr Ser Lys Asn Gln Phe Ser Leu Arg Leu
        90                  95                  100

AGC AGC GTG ACA GCC GCC GAC ACC GCG GTC TAT TAT TGT GCA AGA CAA        389
Ser Ser Val Thr Ala Ala Asp Thr Ala Val Tyr Tyr Cys Ala Arg Gln
    105                 110                 115

GGC ACT ATA GCT GGT ATA CGT CAC TGG GGT CAA GGC AGC CTC GTC ACA        437
Gly Thr Ile Ala Gly Ile Arg His Trp Gly Gln Gly Ser Leu Val Thr
120                 125                 130
```

-continued

| | | |
|---|---|---|
| GTC TCC TCA GCC TCC ACC AAG GGC CCA TCG GTC TTC CCC CTG GCA CCC<br>Val Ser Ser Ala Ser Thr Lys Gly Pro Ser Val Phe Pro Leu Ala Pro<br>135                           140                        145                        150 | 485 |
| TCC TCC AAG AGC ACC TCT GGG GGC ACA GCG GCC CTG GGC TGC CTG GTC<br>Ser Ser Lys Ser Thr Ser Gly Gly Thr Ala Ala Leu Gly Cys Leu Val<br>                            155                        160                        165 | 533 |
| AAG GAC TAC TTC CCC GAA CCG GTG ACG GTG TCG TGG AAC TCA GGC GCC<br>Lys Asp Tyr Phe Pro Glu Pro Val Thr Val Ser Trp Asn Ser Gly Ala<br>              170                        175                        180 | 581 |
| CTG ACC AGC GGC GTG CAC ACC TTC CCG GCT GTC CTA CAG TCC TCA GGA<br>Leu Thr Ser Gly Val His Thr Phe Pro Ala Val Leu Gln Ser Ser Gly<br>            185                        190                        195 | 629 |
| CTC TAC TCC CTC AGC AGC GTG GTG ACC GTG CCC TCC AGC AGC TTG GGC<br>Leu Tyr Ser Leu Ser Ser Val Val Thr Val Pro Ser Ser Ser Leu Gly<br>200                           205                        210 | 677 |
| ACC CAG ACC TAC ATC TGC AAC GTG AAT CAC AAG CCC AGC AAC ACC AAG<br>Thr Gln Thr Tyr Ile Cys Asn Val Asn His Lys Pro Ser Asn Thr Lys<br>215                           220                        225                        230 | 725 |
| GTG GAC AAG AAA GTT GAG CCC AAA TCT TGT GAC AAA ACT CAC ACA TGC<br>Val Asp Lys Lys Val Glu Pro Lys Ser Cys Asp Lys Thr His Thr Cys<br>                            235                        240                        245 | 773 |
| CCA CCG TGC CCA GCA CCT GAA CTC CTG GGG GGA CCG TCA GTC TTC CTC<br>Pro Pro Cys Pro Ala Pro Glu Leu Leu Gly Gly Pro Ser Val Phe Leu<br>            250                        255                        260 | 821 |
| TTC CCC CCA AAA CCC AAG GAC ACC CTC ATG ATC TCC CGG ACC CCT GAG<br>Phe Pro Pro Lys Pro Lys Asp Thr Leu Met Ile Ser Arg Thr Pro Glu<br>            265                        270                        275 | 869 |
| GTC ACA TGC GTG GTG GTG GAC GTG AGC CAC GAA GAC CCT GAG GTC AAG<br>Val Thr Cys Val Val Val Asp Val Ser His Glu Asp Pro Glu Val Lys<br>280                           285                        290 | 917 |
| TTC AAC TGG TAC GTG GAC GGC GTG GAG GTG CAT AAT GCC AAG ACA AAG<br>Phe Asn Trp Tyr Val Asp Gly Val Glu Val His Asn Ala Lys Thr Lys<br>295                           300                        305                        310 | 965 |
| CCG CGG GAG GAG CAG TAC AAC AGC ACG TAC CGT GTG GTC AGC GTC CTC<br>Pro Arg Glu Glu Gln Tyr Asn Ser Thr Tyr Arg Val Val Ser Val Leu<br>                            315                        320                        325 | 1013 |
| ACC GTC CTG CAC CAG GAC TGG CTG AAT GGC AAG GAG TAC AAG TGC AAG<br>Thr Val Leu His Gln Asp Trp Leu Asn Gly Lys Glu Tyr Lys Cys Lys<br>            330                        335                        340 | 1061 |
| GTC TCC AAC AAA GCC CTC CCA GCC CCC ATC GAG AAA ACC ATC TCC AAA<br>Val Ser Asn Lys Ala Leu Pro Ala Pro Ile Glu Lys Thr Ile Ser Lys<br>                            345                        350                        355 | 1109 |
| GCC AAA GGG CAG CCC CGA GAA CCA CAG GTG TAC ACC CTG CCC CCA TCC<br>Ala Lys Gly Gln Pro Arg Glu Pro Gln Val Tyr Thr Leu Pro Pro Ser<br>360                           365                        370 | 1157 |
| CGG GAT GAG CTG ACC AAG AAC CAG GTC AGC CTG ACC TGC CTG GTC AAA<br>Arg Asp Glu Leu Thr Lys Asn Gln Val Ser Leu Thr Cys Leu Val Lys<br>375                           380                        385                        390 | 1205 |
| GGC TTC TAT CCC AGC GAC ATC GCC GTG GAG TGG GAG AGC AAT GGG CAG<br>Gly Phe Tyr Pro Ser Asp Ile Ala Val Glu Trp Glu Ser Asn Gly Gln<br>                            395                        400                        405 | 1253 |
| CCG GAG AAC AAC TAC AAG ACC ACG CCT CCC GTG CTG GAC TCC GAC GGC<br>Pro Glu Asn Asn Tyr Lys Thr Thr Pro Pro Val Leu Asp Ser Asp Gly<br>            410                        415                        420 | 1301 |
| TCC TTC TTC CTC TAC AGC AAG CTC ACC GTG GAC AAG AGC AGG TGG CAG<br>Ser Phe Phe Leu Tyr Ser Lys Leu Thr Val Asp Lys Ser Arg Trp Gln<br>                            425                        430                        435 | 1349 |
| CAG GGG AAC GTC TTC TCA TGC TCC GTG ATG CAT GAG GCT CTG CAC AAC<br>Gln Gly Asn Val Phe Ser Cys Ser Val Met His Glu Ala Leu His Asn<br>            440                        445                        450 | 1397 |

```
CAC TAC ACG CAG AAG AGC CTC TCC CTG TCT CCG GGT AAA TGAGTGCGAC     1446
His Tyr Thr Gln Lys Ser Leu Ser Leu Ser Pro Gly Lys
455                 460                 465

GGCCCCAAGC TT                                                      1458
```

(2) INFORMATION FOR SEQ ID NO:8:

(i) SEQUENCE CHARACTERISTICS:
        (A) LENGTH: 126 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:8:

```
Gln Val Gln Leu Val Glu Ser Gly Gly Gly Val Val Gln Pro Gly Arg
1               5                   10                  15

Ser Leu Arg Leu Ser Cys Ser Ser Gly Phe Ile Phe Ser Ser Tyr
            20                  25                  30

Ala Met Tyr Trp Val Arg Gln Ala Pro Gly Lys Gly Leu Glu Trp Val
            35                  40                  45

Ala Ile Ile Trp Asp Asp Gly Ser Asp Gln His Tyr Ala Asp Ser Val
        50                  55                  60

Lys Gly Arg Phe Thr Ile Ser Arg Asp Asn Ser Lys Asn Thr Leu Phe
65                  70                  75                  80

Leu Gln Met Asp Ser Leu Arg Pro Glu Asp Thr Gly Val Tyr Phe Cys
                85                  90                  95

Ala Arg Asp Gly Gly His Gly Phe Cys Ser Ser Ala Ser Cys Phe Gly
                100                 105                 110

Pro Asp Tyr Trp Gly Gln Gly Thr Pro Val Thr Val Ser Ser
            115                 120                 125
```

(2) INFORMATION FOR SEQ ID NO:9:

(i) SEQUENCE CHARACTERISTICS:
        (A) LENGTH: 817 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:9:

```
AAGCTTATGA ATATGCAAAT CCTCTGAATC TACATGGTAA ATATAGGTTT GTCTATACCA      60

CAAACAGAAA AACATGAGAT CACAGTTCTC TCTACAGTTA CTCAGCACAC AGGACCTCAC     120

CATGGGATGG AGCTGTATCA TCCTCTTCTT GGTAGCAACA GCTACAGGTA AGGGGCTCAC     180

AGTAGCAGGC TTGAGGTCTG GACATATATA TGGGTGACAA TGACATCCAC TTTGCCTTTC     240

TCTCCACAGG TGTCCACTCC CAGGTCCAAC TGGTGGAGTC TGGTGGAGGC GTGGTGCAGC     300

CTGGAAGGTC CCTGAGACTC TCCTGTTCCT CCTCTGGATT CATCTTCAGT AACTATGGCA     360

TGGCCTGGGT CCGCCAGGCT CCAGGCAAGG GGCTGGAGTG GGTCGCAACC ATTAGTCATG     420

ATGGTAGTGA CACTTACTTT CGAGACTCCG TGAAGGGCCG ATTCACTATC TCCAGAGATA     480

ATAGCAAAAA CACCCTATTC CTGCAAATGG ACAGTCTGAG GCCCGAGGAC ACGGGCGTGT     540

ATTTCTGTGC AAGACAAGGG ACTATAGCAG GTATACGTCA CTGGGGCCAA GGGACCCCCG     600

TCACCGTCTC CTCAGGTGAG TCCTTACAAC CTCTCTCTTC TATTCAGCTT AAATAGATTT     660
```

```
TACTGCATTT GTTGGGGGGG AAATGTGTGT ATCTGAATTT CAGGTCATGA AGGACTAGGG      720

ACACCTTGGG AGTCAGAAAG GGTCATTGGG AGCCCGGGCT GATGCAGACA GACATCCTCA      780

GCTCCCAGAC TTCATGGCCA GAGATTTATA GGGATCC                               817
```

(2) INFORMATION FOR SEQ ID NO:10:

(i) SEQUENCE CHARACTERISTICS:
        (A) LENGTH: 731 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:10:

```
AAGCTTTACA GTTACTCAGC ACACAGGACC TCACCATGGG ATGGAGCTGT ATCATCCTCT       60

TCTTGGTAGC AACAGCTACA GGTAAGGGGC TCACAGTAGC AGGCTTGAGG TCTGGACATA      120

TATATGGGTG ACAATGACAT CCACTTTGCC TTTCTCTCCA CAGGTGTCCA CTCCCAGGTC      180

CAACTGGTGG AGTCTGGTGG AGGCGTGGTG CAGCCTGGAA GGTCCCTGAG ACTCTCCTGT      240

TCCTCCTCTG GATTCATCTT CAGTAACTAT GGCATGGCCT GGGTCCGCCA GGCTCCAGGC      300

AAGGGGCTGG AGTGGGTCGC AACCATTAGT CATGATGGTA GTGACACTTA CTTTCGAGAC      360

TCCGTGAAGG GCCGATTCAC TATCTCCAGA GATAATAGCA AAAACACCCT ATTCCTGCAA      420

ATGGACAGTC TGAGGCCCGA GGACACGGGC GTGTATTTCT GTGCAAGACA AGGGACTATA      480

GCAGGTATAC GTCACTGGGG CCAAGGGACC CCCGTCACCG TCTCCTCAGG TGAGTCCTTA      540

CAACCTCTCT CTTCTATTCA GCTTAAATAG ATTTTACTGC ATTTGTTGGG GGGAAATGT       600

GTGTATCTGA ATTTCAGGTC ATGAAGGACT AGGGACACCT TGGGAGTCAG AAAGGGTCAT      660

TGGGAGCCCG GGCTGATGCA GACAGACATC CTCAGCTCCC AGACTTCATG GCCAGAGATT      720

TATAGGGATC C                                                          731
```

(2) INFORMATION FOR SEQ ID NO:11:

(i) SEQUENCE CHARACTERISTICS:
        (A) LENGTH: 817 base pairs
        (B) TYPE: nucleic acid
        (C) STRANDEDNESS: both
        (D) TOPOLOGY: linear (ii) MOLECULE TYPE: cDNA (xi) SEQUENCE DESCRIPTION: SEQ ID NO:11:

```
AAGCTTATGA ATATGCAAAT CCTCTGAATC TACATGGTAA ATATAGGTTT GTCTATACCA       60

CAAACAGAAA AACATGAGAT CACAGTTCTC TCTACAGTTA CTCAGCACAC AGGACCTCAC      120

CATGGGATGG AGCTGTATCA TCCTCTTCTT GGTAGCAACA GCTACAGGTA AGGGGCTCAC      180

AGTAGCAGGC TTGAGGTCTG GACATATATA TGGGTGACAA TGACATCCAC TTTGCCTTTC      240

TCTCCACAGG TGTCCACTCC CAGGTCCAAC TGGTGGAGTC TGGTGGAGGC GTGGTGCAGC      300

CTGGAAGGTC CCTGAGACTC TCCTGTTCCT CCTCTGGATT CATCTTCAGT AACTATGGCA      360

TGGCCTGGGT CCGCCAGGCT CCAGGCAAGG GGCTGGAGTG GGTCGCAACC ATTAGTCATG      420

ATGGTAGTGA CACTTACTTT CGAGACTCCG TGAAGGGCCG ATTCACTATC TCCAGAGATA      480

ATAGCAAAAA CACCCTATTC CTGCAAATGG ACAGTCTGAG GCCCGAGGAC ACGGGCGTGT      540
```

```
ATTTCTGTGC AAGACAAGGG ACTATAGCAG GTATACGTCA CTGGGGCCAA GGGACCACGG     600

TCACCGTCTC CTCAGGTGAG TCCTTACAAC CTCTCTCTTC TATTCAGCTT AAATAGATTT     660

TACTGCATTT GTTGGGGGGG AAATGTGTGT ATCTGAATTT CAGGTCATGA AGGACTAGGG     720

ACACCTTGGG AGTCAGAAAG GGTCATTGGG AGCCCGGGCT GATGCAGACA GACATCCTCA     780

GCTCCCAGAC TTCATGGCCA GAGATTTATA GGGATCC                              817
```

(2) INFORMATION FOR SEQ ID NO:12:

(i) SEQUENCE CHARACTERISTICS:
        (A) LENGTH: 731 base pairs
        (B) TYPE: nucleic acid
        (C) STRANDEDNESS: both
        (D) TOPOLOGY: linear (ii) MOLECULE TYPE: cDNA (iii) HYPOTHETICAL: NO (iv) ANTI-SENSE: NO (xi) SEQUENCE DESCRIPTION: SEQ ID NO:12:

```
AAGCTTTACA GTTACTCAGC ACACAGGACC TCACCATGGG ATGGAGCTGT ATCATCCTCT      60

TCTTGGTAGC AACAGCTACA GGTAAGGGGC TCACAGTAGC AGGCTTGAGG TCTGGACATA     120

TATATGGGTG ACAATGACAT CCACTTTGCC TTTCTCTCCA CAGGTGTCCA CTCCCAGGTC     180

CAACTGGTGG AGTCTGGTGG AGGCGTGGTG CAGCCTGGAA GGTCCCTGAG ACTCTCCTGT     240

TCCTCCTCTG GATTCATCTT CAGTAACTAT GGCATGGCCT GGGTCCGCCA GGCTCCAGGC     300

AAGGGGCTGG AGTGGGTCGC AACCATTAGT CATGATGGTA GTGACACTTA CTTTCGAGAC     360

TCCGTGAAGG GCCGATTCAC TATCTCCAGA GATAATAGCA AAAACACCCT ATTCCTGCAA     420

ATGGACAGTC TGAGGCCCGA GGACACGGGC GTGTATTTCT GTGCAAGACA AGGGACTATA     480

GCAGGTATAC GTCACTGGGG CCAAGGGACC ACGGTCACCG TCTCCTCAGG TGAGTCCTTA     540

CAACCTCTCT CTTCTATTCA GCTTAAATAG ATTTTACTGC ATTTGTTGGG GGGAAATGT      600

GTGTATCTGA ATTTCAGGTC ATGAAGGACT AGGGACACCT TGGGAGTCAG AAAGGGTCAT     660

TGGGAGCCCG GGCTGATGCA GACAGACATC CTCAGCTCCC AGACTTCATG GCCAGAGATT     720

TATAGGGATC C                                                         731
```

(2) INFORMATION FOR SEQ ID NO:13:

(i) SEQUENCE CHARACTERISTICS:
        (A) LENGTH: 11 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:13:

```
Leu Ala Ser Glu Asp Ile Tyr Ser Asp Leu Ala
1               5                   10
```

(2) INFORMATION FOR SEQ ID NO:14:

(i) SEQUENCE CHARACTERISTICS:
        (A) LENGTH: 7 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

Asn Thr Asp Thr Leu Gln Asn
1               5

(2) INFORMATION FOR SEQ ID NO:15:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:15:

Gln Gln Tyr Asn Asn Tyr Pro Trp Thr
1               5

(2) INFORMATION FOR SEQ ID NO:16:

(i) SEQUENCE CHARACTERISTICS:
            (A) LENGTH: 5 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:16:

Asn Tyr Gly Met Ala
1               5

(2) INFORMATION FOR SEQ ID NO:17:

(i) SEQUENCE CHARACTERISTICS:
            (A) LENGTH: 17 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:17:

Thr Ile Ser His Asp Gly Ser Asp Thr Tyr Phe Arg Asp Ser Val Lys
1               5                   10                  15
Gly (2) INFORMATION FOR SEQ ID NO:18:

(i) SEQUENCE CHARACTERISTICS:
            (A) LENGTH: 9 amino acids
            (B) TYPE: amino acid
            (C) STRANDEDNESS: single
            (D) TOPOLOGY: linear (ii) MOLECULE TYPE: peptide (xi) SEQUENCE DESCRIPTION: SEQ ID NO:18:

Gln Gly Thr Ile Ala Gly Ile Arg His
1               5

(2) INFORMATION FOR SEQ ID NO:19:

(i) SEQUENCE CHARACTERISTICS:
            (A) LENGTH: 22 base pairs
            (B) TYPE: nucleic acid

```
        (C) STRANDEDNESS: single
        (D) TOPOLOGY: linear (ii) MOLECULE TYPE: cDNA (xi) SEQUENCE DESCRIPTION: SEQ ID NO:19:

GTTAGATCTC CAGCTTGGTC CC                                            22

(2) INFORMATION FOR SEQ ID NO:20:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:20:

TGAGGAGACG GTGACCGTGG TCCCTTGGCC                                    30

(2) INFORMATION FOR SEQ ID NO:21:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

GACATTCAGC TGACCCAGTC TCCA                                          24

(2) INFORMATION FOR SEQ ID NO:22:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:22:

AGGTSMARCT GCAGSAGTCW GG                                            22

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

GTTTCATAAT ATTGGAGACA                                               20

(2) INFORMATION FOR SEQ ID NO:24:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: cDNA
```

(xi) SEQUENCE DESCRIPTION: SEQ ID NO:24:

AGAGTGACCA TCACCTGTCT AGCAAGTGAG GACATTTACA GTGATTTAGC ATGGTACCAG    60

CAGAAGCCA    69

(2) INFORMATION FOR SEQ ID NO:25:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

CTGCTGATCT ACAATACAGA TACCTTGCAA AATGGTGTGC CAAGCAGATT C    51

(2) INFORMATION FOR SEQ ID NO:26:

(i) SEQUENCE CHARACTERISTICS:
        (A) LENGTH: 60 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

ATCGCCACCT ACTACTGCCA ACAGTATAAC AATTATCCGT GGACGTTCGG CCAAGGGACC    60

(2) INFORMATION FOR SEQ ID NO:27:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

TCTGGCTTCA CCTTCACCAA CTATGGCATG GCCTGGGTGA GACAGCCACC T    51

(2) INFORMATION FOR SEQ ID NO:28:

(i) SEQUENCE CHARACTERISTICS:
        (A) LENGTH: 75 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

GGTCTTGAGT GGATTGGAAC CATTAGTCAT GATGGTAGTG ACACTTACTT TCGAGACTCT    60

GTGAAGGGGA GAGTG    75

(2) INFORMATION FOR SEQ ID NO:29:

(i) SEQUENCE CHARACTERISTICS:
        (A) LENGTH: 63 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

GTCTATTATT GTGCAAGACA AGGCACTATA GCTGGTATAC GTCACTGGGG TCAAGGCAGC        60

CTC                                                                    63

(2) INFORMATION FOR SEQ ID NO:30:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

GCTTCACCTT CAGCAACTAT GGCAT                                            25

(2) INFORMATION FOR SEQ ID NO:31:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

CACTCCCAGG TCCAACTGGT GGAGTCTGGT GGAGGCGTGG TGCAGCCTGG                  50

(2) INFORMATION FOR SEQ ID NO:32:

(i) SEQUENCE CHARACTERISTICS:
        (A) LENGTH: 58 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

AAGGTCCCTG AGACTCTCCT GTTCCTCCTC TGGATTCATC TTCAGTAACT ATGGCATG         58

(2) INFORMATION FOR SEQ ID NO:33:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:33:

GTCCGCCAGG CTCCAGGCAA GGGGCTGGAG TGG                                    33

(2) INFORMATION FOR SEQ ID NO:34:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:34:

```
ACTATCTCCA GAGATAATAG CAAAAACACC CTATTCCTGC AAATGG                    46

(2) INFORMATION FOR SEQ ID NO:35:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:35:

ACAGTCTGAG GCCCGAGGAC ACGGGCGTGT ATTTCTGTGC AAGACAAGGG AC             52

(2) INFORMATION FOR SEQ ID NO:36:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:36:

TGGGGCCAAG GGACCCCCGT CACCGTCTCC TCA                                  33

(2) INFORMATION FOR SEQ ID NO:37:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:37:

AGCTTTACAG TTACTGAGCA CACAGGACCT CAC                                  33

(2) INFORMATION FOR SEQ ID NO:38:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:38:

CATGGTGAGG TCCTGTGTGC TCAGTAACTG TAA                                  33

(2) INFORMATION FOR SEQ ID NO:39:

(i) SEQUENCE CHARACTERISTICS:
        (A) LENGTH: 137 amino acids
        (B) TYPE: amino acid
        (D) TOPOLOGY: linear (ii) MOLECULE TYPE: protein (xi) SEQUENCE DESCRIPTION: SEQ ID NO:39:

Met Gly Trp Ser Cys Ile Ile Leu Phe Leu Val Ala Thr Ala Thr Gly
  1               5                  10                  15

Val His Ser Gln Val Gln Leu Val Glu Ser Gly Gly Gly Val Val Gln
```

```
                        20                  25                  30
Pro Gly Arg Ser Leu Arg Leu Ser Cys Ser Ser Ser Gly Phe Ile Phe
            35                  40                  45
Ser Asn Tyr Gly Met Ala Trp Val Arg Gln Ala Pro Gly Lys Gly Leu
        50                  55                  60
Glu Trp Val Ala Thr Ile Ser His Asp Gly Ser Asp Thr Tyr Phe Arg
 65                  70                  75                  80
Asp Ser Val Lys Gly Arg Phe Thr Ile Ser Arg Asp Asn Ser Lys Asn
                85                  90                  95
Thr Leu Phe Leu Gln Met Asp Ser Leu Arg Pro Glu Asp Thr Gly Val
            100                 105                 110
Tyr Phe Cys Ala Arg Gln Gly Thr Ile Ala Gly Ile Arg His Trp Gly
        115                 120                 125
Gln Gly Thr Pro Val Thr Val Ser Ser
    130                 135
```

(2) INFORMATION FOR SEQ ID NO:40:

(i) SEQUENCE CHARACTERISTICS:
        (A) LENGTH: 137 amino acids
        (B) TYPE: amino acid
        (D) TOPOLOGY: linear (ii) MOLECULE TYPE: protein (xi) SEQUENCE DESCRIPTION: SEQ ID NO:40:

```
Met Gly Trp Ser Cys Ile Ile Leu Phe Leu Val Ala Thr Ala Thr Gly
 1               5                  10                  15
Val His Ser Gln Val Gln Leu Val Glu Ser Gly Gly Gly Val Val Gln
                20                  25                  30
Pro Gly Arg Ser Leu Arg Leu Ser Cys Ser Ser Ser Gly Phe Ile Phe
            35                  40                  45
Ser Asn Tyr Gly Met Ala Trp Val Arg Gln Ala Pro Gly Lys Gly Leu
        50                  55                  60
Glu Trp Val Ala Thr Ile Ser His Asp Gly Ser Asp Thr Tyr Phe Arg
 65                  70                  75                  80
Asp Ser Val Lys Gly Arg Phe Thr Ile Ser Arg Asp Asn Ser Lys Asn
                85                  90                  95
Thr Leu Phe Leu Gln Met Asp Ser Leu Arg Pro Glu Asp Thr Gly Val
            100                 105                 110
Tyr Phe Cys Ala Arg Gln Gly Thr Ile Ala Gly Ile Arg His Trp Gly
        115                 120                 125
Gln Gly Thr Thr Val Thr Val Ser Ser
    130                 135
```

(2) INFORMATION FOR SEQ ID NO:41:

(i) SEQUENCE CHARACTERISTICS:
        (A) LENGTH: 467 amino acids
        (B) TYPE: amino acid
        (D) TOPOLOGY: linear (ii) MOLECULE TYPE: protein (xi) SEQUENCE DESCRIPTION: SEQ ID NO:41:

```
Met Gly Trp Ser Cys Ile Ile Leu Phe Leu Val Ala Thr Ala Thr Gly
 1               5                  10                  15
Val His Ser Gln Val Gln Leu Gln Glu Ser Gly Pro Gly Leu Val Arg
                20                  25                  30
```

-continued

```
Pro Ser Gln Thr Leu Ser Leu Thr Cys Thr Val Ser Gly Phe Thr Phe
            35                  40                  45

Thr Asn Tyr Gly Met Ala Trp Val Arg Gln Pro Pro Gly Arg Gly Leu
        50                  55                  60

Glu Trp Ile Gly Thr Ile Ser His Asp Gly Ser Asp Thr Tyr Phe Arg
 65                  70                  75                  80

Asp Ser Val Lys Gly Arg Val Thr Met Leu Val Asp Thr Ser Lys Asn
                85                  90                  95

Gln Phe Ser Leu Arg Leu Ser Ser Val Thr Ala Ala Asp Thr Ala Val
            100                 105                 110

Tyr Tyr Cys Ala Arg Gln Gly Thr Ile Ala Gly Ile Arg His Trp Gly
        115                 120                 125

Gln Gly Ser Leu Val Thr Val Ser Ser Ala Ser Thr Lys Gly Pro Ser
    130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
    210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
    290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
        355                 360                 365

Tyr Thr Leu Pro Pro Ser Arg Asp Glu Leu Thr Lys Asn Gln Val Ser
    370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
        435                 440                 445
```

-continued

```
His Glu Ala Leu His Asn His Tyr Thr Gln Lys Ser Leu Ser Leu Ser
    450                 455                 460

Pro Gly Lys
465

(2) INFORMATION FOR SEQ ID NO:42:

(i) SEQUENCE CHARACTERISTICS:
        (A) LENGTH: 467 amino acids
        (B) TYPE: amino acid
        (D) TOPOLOGY: linear (ii) MOLECULE TYPE: protein (xi) SEQUENCE DESCRIPTION: SEQ ID NO:42:

Met Gly Trp Ser Cys Ile Ile Leu Phe Leu Val Ala Thr Ala Thr Gly
  1               5                  10                  15

Val His Ser Gln Val Gln Leu Gln Glu Ser Gly Pro Gly Leu Val Arg
                 20                  25                  30

Pro Ser Gln Thr Leu Ser Leu Thr Cys Thr Val Ser Gly Phe Thr Phe
             35                  40                  45

Ser Asn Tyr Gly Met Ala Trp Val Arg Gln Pro Pro Gly Arg Gly Leu
         50                  55                  60

Glu Trp Ile Gly Thr Ile Ser His Asp Gly Ser Asp Thr Tyr Phe Arg
 65                  70                  75                  80

Asp Ser Val Lys Gly Arg Val Thr Met Leu Val Asp Thr Ser Lys Asn
                 85                  90                  95

Gln Phe Ser Leu Arg Leu Ser Ser Val Thr Ala Ala Asp Thr Ala Val
                100                 105                 110

Tyr Tyr Cys Ala Arg Gln Gly Thr Ile Ala Gly Ile Arg His Trp Gly
            115                 120                 125

Gln Gly Ser Leu Val Thr Val Ser Ser Ala Ser Thr Lys Gly Pro Ser
        130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Ser Leu Gly Thr Gln Thr Tyr Ile Cys Asn Val Asn His
210                 215                 220

Lys Pro Ser Asn Thr Lys Val Asp Lys Lys Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
        275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
```

-continued

```
            325                 330                 335
Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Arg Asp Glu Leu Thr Lys Asn Gln Val Ser
            370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                    405                 410                 415

Val Leu Asp Ser Asp Gly Ser Phe Phe Leu Tyr Ser Lys Leu Thr Val
                    420                 425                 430

Asp Lys Ser Arg Trp Gln Gln Gly Asn Val Phe Ser Cys Ser Val Met
                    435                 440                 445

His Glu Ala Leu His Asn His Tyr Thr Gln Lys Ser Leu Ser Leu Ser
                    450                 455                 460

Pro Gly Lys
465
```

(2) INFORMATION FOR SEQ ID NO:43:

(i) SEQUENCE CHARACTERISTICS:
        (A) LENGTH: 233 amino acids
        (B) TYPE: amino acid
        (D) TOPOLOGY: linear (ii) MOLECULE TYPE: protein (xi) SEQUENCE DESCRIPTION: SEQ ID NO:43:

```
Met Gly Trp Ser Cys Ile Ile Leu Phe Leu Val Ala Thr Ala Thr Gly
1               5                   10                  15

Val His Ser Asp Ile Gln Met Thr Gln Ser Pro Ser Ser Leu Ser Ala
                20                  25                  30

Ser Val Gly Asp Arg Val Thr Ile Thr Cys Leu Ala Ser Glu Asp Ile
            35                  40                  45

Tyr Ser Asp Leu Ala Trp Tyr Gln Gln Lys Pro Gly Lys Ala Pro Lys
        50                  55                  60

Leu Leu Ile Tyr Asn Thr Asp Thr Leu Gln Asn Gly Val Pro Ser Arg
65                  70                  75                  80

Phe Ser Gly Ser Gly Ser Gly Thr Asp Phe Thr Phe Thr Ile Ser Ser
                85                  90                  95

Leu Gln Pro Glu Asp Ile Ala Thr Tyr Tyr Cys Gln Gln Tyr Asn Asn
            100                 105                 110

Tyr Pro Trp Thr Phe Gly Gln Gly Thr Lys Val Glu Ile Lys Arg Thr
        115                 120                 125

Val Ala Ala Pro Ser Val Phe Ile Phe Pro Pro Ser Asp Glu Gln Leu
    130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
        195                 200                 205
```

```
Lys Val Tyr Ala Cys Glu Val Thr His Gln Gly Leu Ser Ser Pro Val
    210                 215                 220

Thr Lys Ser Phe Asn Arg Gly Glu Cys
225                 230
```